US012343055B1

(12) United States Patent
Antonacci et al.

(10) Patent No.: US 12,343,055 B1
(45) Date of Patent: Jul. 1, 2025

(54) ANCHOR DEVICE FOR BONE IMPLANTATION DURING SURGICAL PROCEDURES

(71) Applicant: Institute for Spine & Scoliosis, P.A., Lawrenceville, NJ (US)

(72) Inventors: Mark Darryl Antonacci, Skillman, NJ (US); Matthew L. Cavuto, London (GB); Anthony C. Antonacci, Ridgefield, CT (US)

( * ) Notice: Subject to any disclaimer, the term of this patent is extended or adjusted under 35 U.S.C. 154(b) by 0 days.

(21) Appl. No.: 18/910,337

(22) Filed: Oct. 9, 2024

Related U.S. Application Data

(60) Provisional application No. 63/678,827, filed on Aug. 2, 2024.

(51) Int. Cl.
*A61B 17/84* (2006.01)

(52) U.S. Cl.
CPC .................. *A61B 17/846* (2013.01)

(58) Field of Classification Search
CPC .............. A61B 17/846; A61B 17/7049; A61B 17/7002; A61B 17/7019; A61B 17/7004; A61B 17/701; A61B 17/7011; A61B 17/7014; A61B 17/7025
USPC .................................................. 606/250–279
See application file for complete search history.

(56) References Cited

U.S. PATENT DOCUMENTS

| | | | | |
|---|---|---|---|---|
| 5,496,321 A | * | 3/1996 | Puno | A61B 17/7091 606/305 |
| 5,584,831 A | * | 12/1996 | McKay | A61B 17/7077 606/86 A |
| 6,478,798 B1 | * | 11/2002 | Howland | A61B 17/7041 606/279 |
| 7,166,109 B2 | * | 1/2007 | Biedermann | A61B 17/7037 606/279 |
| 7,819,899 B2 | | 10/2010 | Lancial | |
| 7,922,748 B2 | | 4/2011 | Hoffman | |
| 8,034,085 B2 | | 10/2011 | Slivka et al. | |
| 8,052,720 B2 | | 11/2011 | Kuester et al. | |
| 8,177,810 B2 | | 5/2012 | Ferree | |
| 8,641,736 B2 | | 2/2014 | Marik et al. | |
| 9,345,517 B2 | | 5/2016 | Zhang et al. | |
| 9,463,048 B2 | | 10/2016 | Iott et al. | |
| 9,526,526 B2 | | 12/2016 | Zhang et al. | |
| 9,532,810 B2 | | 1/2017 | Hestad et al. | |
| 10,278,736 B2 | | 5/2019 | Samdani et al. | |
| 11,464,547 B2 | | 10/2022 | Biyani et al. | |
| 11,684,394 B2 | | 6/2023 | Nichols et al. | |
| 2008/0009863 A1 | | 1/2008 | Bond et al. | |

(Continued)

*Primary Examiner* — Eduardo C Robert
*Assistant Examiner* — Tara Rose E Carter
(74) *Attorney, Agent, or Firm* — Sutton Magidoff Barkume LLP

(57) ABSTRACT

Provided herein are several embodiments for an anchor device for insertion into a bone, all of which include a post suitable for implantation into a bone, and a cord housing coupled to the post. The cord housing has a lower housing with a cradle for receiving therein at least one cord, and an upper housing with a clamp for placement over the at least one cord inserted into the cradle. The joining of the upper housing to the lower housing forms a cord channel by the cradle and the clamp, to encase the at least one cord placed into the cradle. The cord housing also has means for fastening the upper housing to the lower housing and securing the at least one cord within the cord channel.

36 Claims, 21 Drawing Sheets

(56) References Cited

U.S. PATENT DOCUMENTS

| | | |
|---|---|---|
| 2011/0208254 A1 | 8/2011 | Villa et al. |
| 2020/0078051 A1 | 3/2020 | Faulhaber |
| 2020/0297389 A1 | 9/2020 | Shluzas et al. |
| 2020/0323562 A1 | 10/2020 | Hoernschemeyer et al. |
| 2022/0110662 A1 | 4/2022 | LaColla |
| 2023/0190336 A1 | 6/2023 | Leff et al. |
| 2023/0310037 A1 | 10/2023 | Glerum et al. |

\* cited by examiner

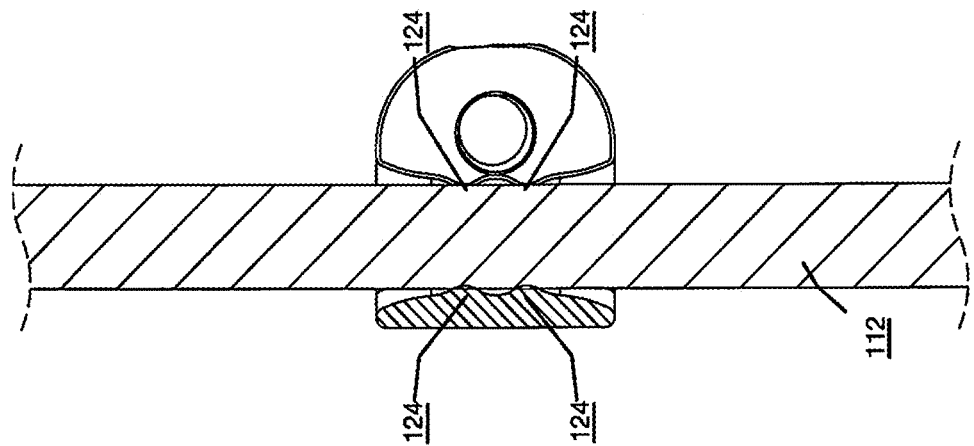
FIG. 9
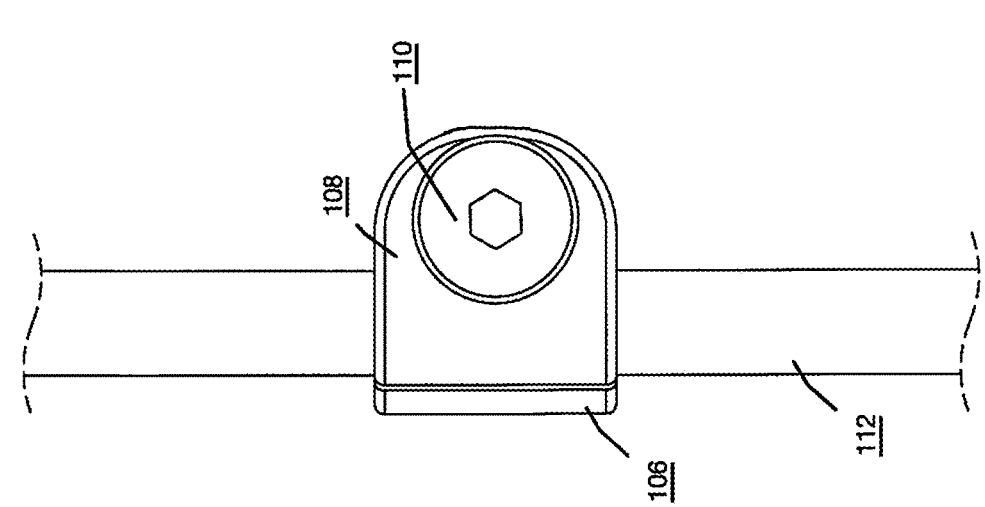
FIG. 8A
FIG. 8

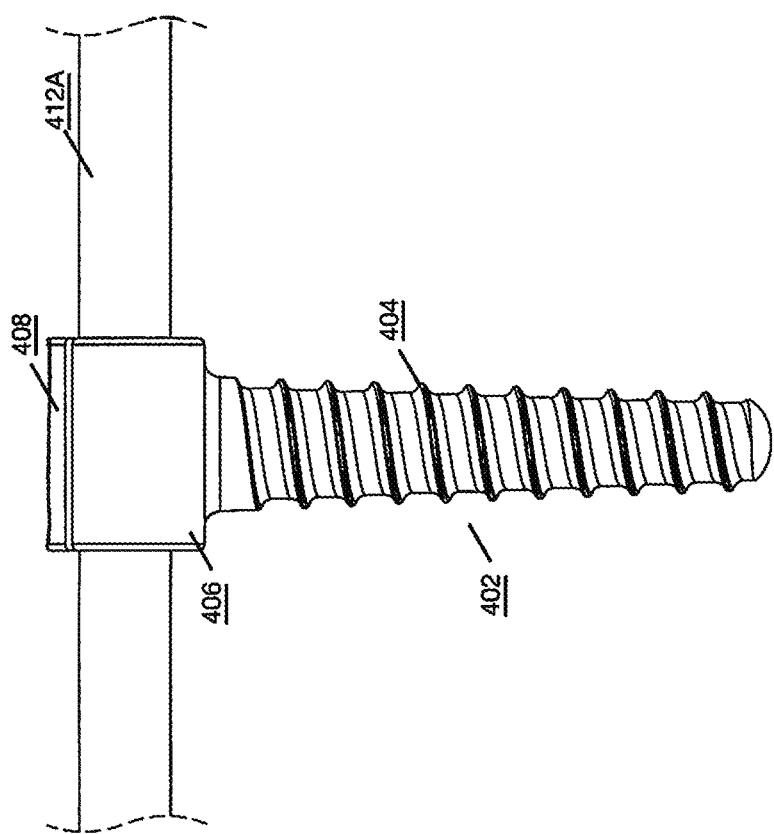

ANCHOR DEVICE FOR BONE IMPLANTATION DURING SURGICAL PROCEDURES

TECHNICAL FIELD

This application relates to improved anchor devices for implantation into a bone such as a vertebra during spinal correction surgery, such as for the correction of scoliosis using non fusion or modified fusion anterior scoliosis correction, and for other spinal abnormalities.

BACKGROUND OF THE INVENTION

Recent developments in scoliosis treatment, referred to generally as vertebral body tethering (VBT), is a non-fusion surgery that has been found to provide advantages over bracing and fusion techniques of the prior art. In particular, recent advances have been made in de-rotation procedures, as taught in U.S. Pat. No. 11,547,452 METHOD FOR IMPROVED SPINAL CORRECTION SURGERY IMPLEMENTING NON-FUSION ANTERIOR SCOLIOSIS CORRECTION TECHNIQUES WITH VERTEBRAE DE-ROTATION. As explained in the '452 patent, which is incorporated by reference herein, a plurality of anchor devices are inserted onto various vertebral bodies of the patient, via a mini-opening in the patient and/or a portal. Each anchor device has a channel disposed therein, such that a cord or tether may be placed into the channels. One end of the tether is secured within a corresponding anchor device.

Then, a de-rotation vertebrae adjustment procedure is performed, as explained in the '452 patent. After this de-rotation maneuver is performed, then the cord is tensioned in the channel of the second anchor screw, and the tensioned cord is secured in the channel of the second anchor screw in order to maintain the de-rotation.

Thus, the cord is tensioned so as to urge the other channels in which the cord is disposed, along with the corresponding vertebral bodies, towards a straighter orientation. The cord is secured in all the channels using a tensioner, thus urging the spine towards correction of the scoliosis condition with de-rotation and compression or other dimensionality. Optionally, the cord may be adjusted during a subsequent follow-up procedure so as to continue to correct the scoliosis condition over a greater period of time. This is particularly beneficial to younger patients whose spine is still growing. The patient often can leave the hospital within a few days of the surgery and may be able to return to normal activities, including athletic activities, within six weeks or so.

The anchor devices required for this anterior scoliosis correction and other VBT procedures that are available in the prior art suffer from several disadvantages. These anchor devices were initially designed to be used with rigid metal rods, rather than a flexible cord/tether as is now done in modern anterior scoliosis correction and/or VBT procedures, and they have been found to cause wearing and eventual breakage in the flexible cords as they tend to rub against the anchor device due to being urged in a non-linear manner along the deformed spine. Another problem in current anchor devices is the manner in which the cord is held in place after being tightened; again, due to the design for use with a rigid rod rather than a flexible cord, which also causes premature wear and tear. The current anchor devices are also bulky and rough edged due to design adaptations from rigid metal rod concepts and are known to potentially cause local tissue erosion in select cases as well as cord breakage. In addition, modern anterior scoliosis correction techniques incorporate non-fusion and modified fusion principles and may utilize multiple cords (two or more), thus necessitating use of additional anchor devices in the patient's spine in order to support the multiple cords (see the '452 patent) that may not have enough bone mass to provide adequate support.

These problems are addressed by the anchor devices of the present invention as will now be described.

SUMMARY OF THE INVENTION

Provided herein are several embodiments for an anchor device for insertion into a bone, all of which includes a post suitable for implantation into a bone, and a cord housing coupled to the post. The cord housing has a lower housing with a cradle for receiving therein at least one cord, and an upper housing with a clamp for placement over the at least one cord inserted into the cradle. The joining of the upper housing to the lower housing forms a cord channel by the cradle and the clamp, to encase the at least one cord placed into the cradle. The cord housing also has means for fastening the upper housing to the lower housing and securing the at least one cord within the cord channel.

The lower housing has a lower housing major surface; and the upper housing has an upper housing major surface. The upper housing major surface substantially abuts the lower housing major surface when the upper housing is joined to the lower housing and provides a stop to prevent overtightening of the upper housing to the lower housing. In one example, the lower housing major surface may be flat, in which case the upper housing major surface may then also be flat.

The lower housing has a lower housing minor surface; and the upper housing has an upper housing minor surface. The upper housing minor surface substantially abuts the lower housing minor surface when the upper housing is joined to the lower housing and provides a stop to prevent overtightening of the upper housing to the lower housing. As with the major surfaces, the lower housing minor surface may be flat, and the upper housing minor surface may then also be flat.

Although the major and minor surfaces of both the upper housing and the lower housing are preferably flat, they may have other shapes that are designed to align and mate with each other, such as a V-shaped channel.

The abutment of the upper housing minor surface to the lower housing minor surface also improves alignment of the upper housing and lower housing wherein the upper housing is prevented from rotating and spinning about an axis when the housings are adjoined together.

The cord channel is formed by adjoining the upper housing major surface to the lower housing major surface, the upper housing minor surface to the lower housing minor surface, and the clamp over the cradle. Then the at least one cord encased within the cord channel is partially compressed by the adjoining of the clamp to the cradle.

The adjoining of the upper housing major surface to the lower housing major surface and the upper housing minor surface to the lower housing minor surface provides a limit to the compression of the at least one cord by the clamp and the cradle.

The cradle of the lower housing may have a first end portion, a middle portion, and a second end portion, wherein the first end portion and the second end portion are outwardly flared; and the clamp of the upper housing may likewise have a first end portion, a middle portion, and a second end portion, wherein the first end portion and the second end portion are outwardly flared.

The middle portion of the cradle may have a non-smooth surface, such as but not limited to a plurality of ribs, suitable for gripping the cord when placed therein. Similarly, the middle portion of the clamp may have a non-smooth surface, such as but not limited to a plurality of ribs, suitable for gripping the cord when placed over the cradle. In the alternative to ribs, other non-smooth surfaces such as dimples or a roughened texture such as knurling may be used.

The means for fastening may include a threaded fastener (such as a screw with a head); in which case the lower housing has a receiving cylindrical portion comprising threads suitable for receiving the threaded fastener, and the upper housing further has an aperture for receiving therethrough the threaded fastener. The aperture may be countersunk to allow the head of the screw to be substantially flush with the upper housing. The screw may be a separate part, or it may be captively associated with the upper housing.

In particular, in one embodiment, the anchor device is suitable for encasing a single cord, wherein the cradle is partially cylindrical and adapted to receive a single cord; the clamp is partially cylindrical and adapted for placement over the single cord inserted into the cradle; and the cord channel formed by clamp and the cradle when the upper housing is joined to the lower housing is substantially cylindrical to encase a single cord placed into the cradle. In this embodiment, the cradle provides a cross-sectional profile of greater than half of the cylinder and the clamp provides a cross-sectional profile of less than half of the cylinder, so that the cord may be press fit into the cradle and held in place temporarily until the upper housing is joined to the lower housing.

A second and a third alternative embodiment are described that are each suitable for encasing at least a pair of cords, in which the cradle is adapted to receive at least two cords; the clamp is adapted for placement over the at least two cords inserted into the cradle; and the cord channel formed by clamp and the cradle when the upper housing is joined to the lower housing encases the at least two cords placed into the cradle.

For example, the cord channel formed by the clamp and the cradle may be an elongated cylinder adapted to encase the at least two cords side by side. In this case, the cradle may provide a cross-sectional profile of greater than half of the elongated cylinder and the clamp provides a cross-sectional profile of less than half of the elongated cylinder. This enables the cords to be press fit into the cradle and held in place temporarily until the upper housing is joined to the lower housing.

In particular, in the second alternative embodiment, the at least two cords are placed within the cradle side by side on a horizontal axis; and in the third alternative embodiment, the at least two cords are placed within the cradle side by side on a vertical axis. Alternatively, the at least two cords are placed within the cradle diagonally, offset from a vertical axis and a horizontal axis.

As in the first embodiment, the cradle may have a first end portion, a middle portion, and a second end portion, wherein the first end portion and the second end portion are outwardly flared. Similarly, the clamp may have a first end portion, a middle portion, and a second end portion, wherein the first end portion and the second end portion are outwardly flared.

The middle portion of the cradle may have a non-smooth surface, such as but not limited to a plurality of ribs, suitable for gripping the cords when placed therein. Similarly, the middle portion of the clamp may have a non-smooth surface, such as but not limited to a plurality of ribs, suitable for gripping the cords when placed over the cradle. In the alternative to ribs, other non-smooth surfaces such as dimples or a roughened texture such as knurling may be used.

A fourth alternative embodiment is also described that is also suitable for encasing at least a pair of cords in a varied construction than the first three embodiments. In this fourth embodiment, the anchor device similarly has a post suitable for implantation into a bone, and a cord housing coupled to the post. However, in this fourth embodiment, the cord housing has a lower housing comprising at least a pair of cradles, each of the cradles for receiving therein at least one cord. The cord housing also has an upper housing having at least a pair of clamps, each of the clamps for placement over each cord inserted into each cradle. The joining of the upper housing to the lower housing thus forms at least a pair of cord channels by the cradles and the clamps, to encase in each cord channel the cord or cords placed into each of the cradles. The cord housing also has means for fastening the upper housing to the lower housing and securing the cords within the cord channels.

In this embodiment, the lower housing has a lower housing major surface located optionally between the cradles; and the upper housing has an upper housing major surface located optionally between the clamps. The upper housing major surface substantially abuts the lower housing major surface when the upper housing is joined to the lower housing and provides a stop to prevent overtightening of the upper housing to the lower housing. In one example, the lower housing major surface may be flat, and the upper housing major surface may then also be flat.

The lower housing may have a pair of lower housing minor surfaces; and the upper housing may have a pair of upper housing minor surfaces. The upper housing minor surfaces substantially abut the lower housing minor surfaces when the upper housing is joined to the lower housing and provide a stop to prevent overtightening of the upper housing to the lower housing. As with the major surfaces, the lower housing minor surfaces may be flat, and the upper housing minor surfaces may then also be flat.

Although the major and minor surfaces are preferably flat, they may have other shapes that are designed to align and mate with each other, such as a V-shaped channel.

The abutment of the upper housing minor surfaces to the lower housing minor surfaces also improves alignment of the upper housing and lower housing wherein the upper housing is prevented from rotating and spinning about an axis.

The cord channels are formed by adjoining the upper housing major surface to the lower housing major surface, the upper housing minor surfaces to the lower housing minor surfaces, and the clamps to the cradles. The cords encased within the cord channels are partially compressed by the clamps and the cradles.

The adjoining of the upper housing major surface to the lower housing major surface and the upper housing minor surfaces to the lower housing minor surfaces provide a limit to the compression of the cords by the clamps and the cradles.

Each of the cradles may have a first end portion, a middle portion, and a second end portion, wherein the first end portion and the second end portion are outwardly flared; and each of the clamps may have a first end portion, a middle portion, and a second end portion, wherein the first end portion and the second end portion are outwardly flared.

The middle portion of each cradle may have a non-smooth surface, such as but not limited to a plurality of ribs, suitable for gripping the cord. Similarly, the middle portion of each clamp may have a non-smooth surface, such as but not limited to a plurality of ribs, suitable for gripping the cord. In the alternative to ribs, other non-smooth surfaces such as dimples or a roughened texture may be used.

The means for fastening may include a threaded fastener (such as a screw with a head); in which case the lower housing has a receiving cylindrical portion comprising threads suitable for receiving the threaded fastener, and the upper housing further has an aperture for receiving therethrough the threaded fastener. The aperture may be countersunk to allow the head of the screw to be substantially flush with the upper housing. The screw may be a separate part, or it may be captively associated with the upper housing.

BRIEF DESCRIPTION OF THE DRAWING

FIG. 8 is a top view of the first embodiment of FIG. 1.

FIG. 8A is a top view of the first embodiment of FIG. 1 with the cord pressed into the lower housing and the upper housing not present.

FIG. 9 is a top cross section view of the first embodiment of FIG. 1.

FIG. 33 is a front view of the fourth embodiment of FIG. 28.

DETAILED DESCRIPTION OF THE INVENTION

The present invention is an improved anchor device, useful for example in surgical techniques wherein the anchor device is inserted into a bone of a patient during scoliosis correction surgery and the like. As explained above, an anchor device in the prior art is inserted into several vertebrae, through which a device such as a tether, cord or band is inserted and secured to enable the surgeon to impart various forces along the spine in an effort to correct for scoliosis or kyphosis. It is noted that when the term "cord" is used herein, it is intended to include other types of flexible devices such as straps, tethers, bands, cables and the like.

Figure 1A:
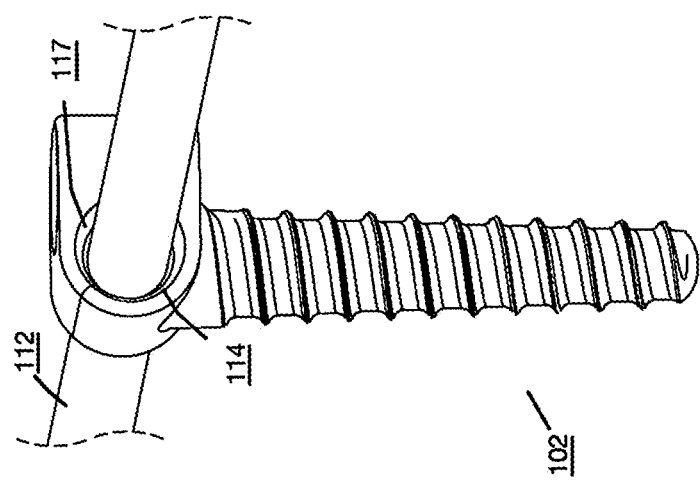
FIG. 1A is an alternative perspective view of the first embodiment of FIG. 1.
Figure 1:
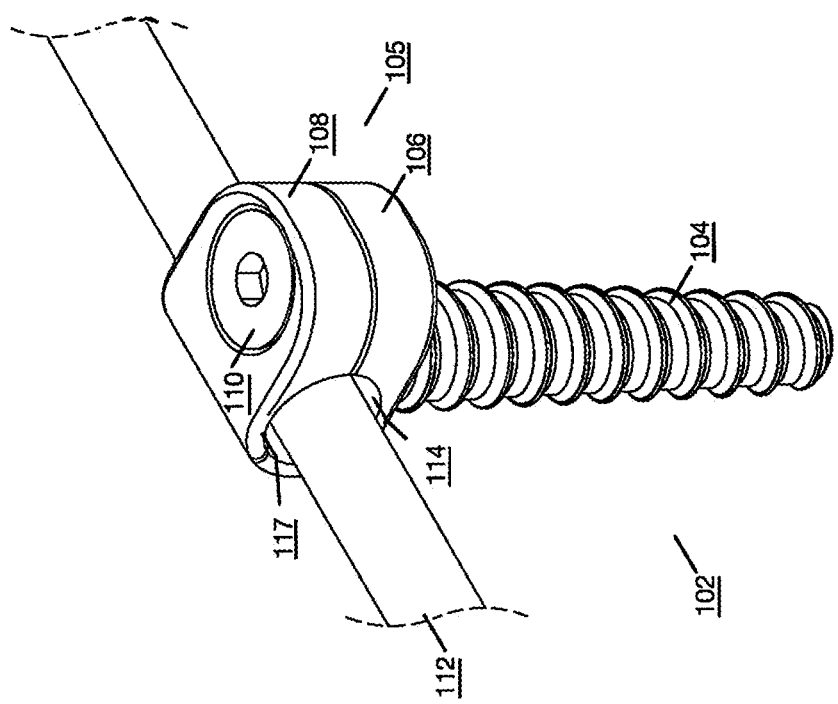
FIG. 1 is a first perspective view of a first embodiment of the anchor device of the present invention suitable for a single cord or band.
Figure 2:
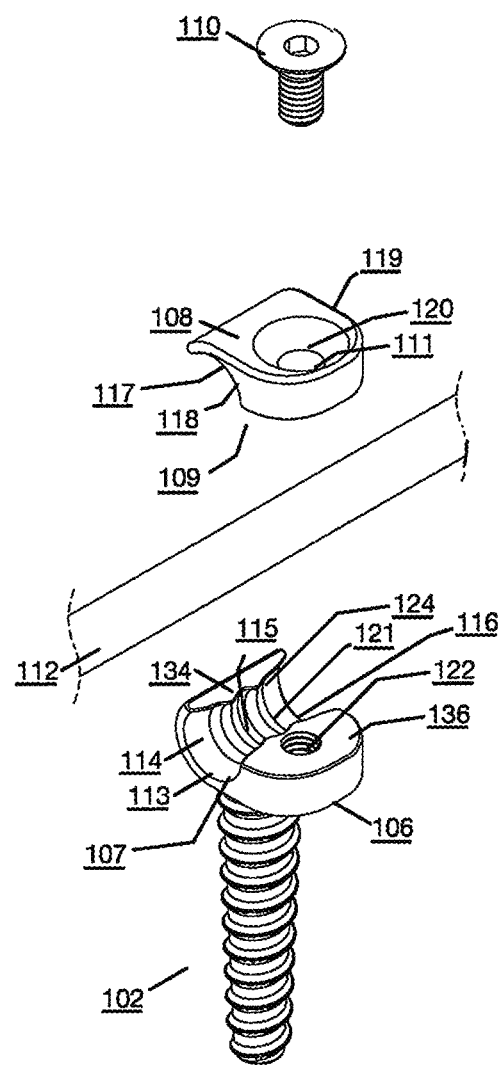
FIG. 2 is an exploded perspective view of the first embodiment of FIG. 1.
Figure 39:
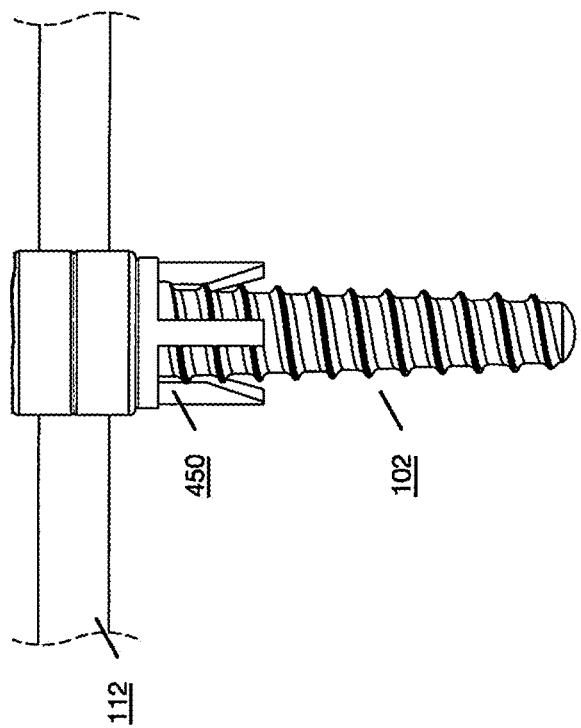
FIG. 39 is a side view of the anchor device of the first preferred embodiment of the invention inserted into the prior art staple of FIG. 38.
Figure 38:
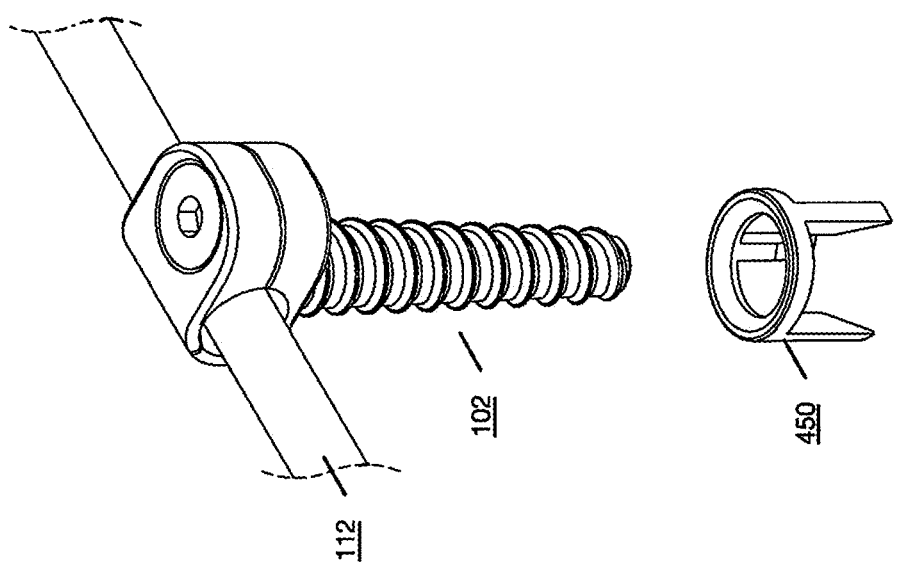
FIG. 38 is a perspective view of a prior art staple with the anchor device of the first preferred embodiment of the invention.

With reference to FIGS. 1, 1A and 2, the first embodiment of the anchor device, suitable for implementation with a single cord, is shown. The anchor device 102 includes a threaded post 104 suitable for implantation into a bone as known in the art, and a cord housing 105 that is coupled to the post. The cord housing 105 maybe fixedly coupled to the post 104 as shown, so that the connection is rigid and unmoving, or the cord housing may be rotatably or otherwise movably coupled to the post. Shown in FIGS. 38 and 39 is a bone anchoring staple 450, as well known in the art, that may be utilized with the anchor device of the present invention.

The cord housing 105 is formed from two major components, i.e., a lower housing 106 and an upper housing 108. The lower housing 106 has a cradle 107 for receiving a cord, and the upper housing has a clamp 109 for placement over a cord 112 inserted into the cradle 107. In this single cord embodiment, the cradle 107 is partially cylindrical and adapted to receive a single cord, and the clamp is also partially cylindrical and adapted to be placed over a cord that has been inserted into the cradle. As such, the lower housing 106 and the upper housing 108 are joined together around a cord 112 during use to form a substantially cylindrical cord channel 113 by the cradle 107 and the clamp 109, to encase a cord placed into the cradle. Means for fastening the upper housing 108 to the lower housing 106 and securing the cord within the cord channel 113 may be, for example, a fastener 110. The fastener 110 in the preferred embodiment is a bolt, screw, or other type of device that can removably attach and fasten the upper housing to the lower housing. The threaded post 104 is inserted and threaded into the bone of the patient by the surgeon as known in the art, for example into a vertebra of a patient's spine during a procedure for correcting a scoliosis curve.

It is noted that in the prior art, a set screw is typically used to hold directly and impinge upon the cord in place within the corresponding anchor device. A set screw in this context is used to impart force on the cord directly to hold it in place. However, the fastener 110 in the preferred embodiment of the present invention does not impinge directly and impart direct force upon the cord. Instead, the fastener 110 is inserted through an aperture 111 in the upper housing 108 and threaded into the threaded aperture 122 in the lower housing 106. The fastener 110 is then tightened as desired so that the upper housing 108 compresses against the cord 112 within the channel 113 in order to keep the cord 112 clamped in and held snugly in place. As shown, in the preferred embodiment, the head of the fastener 110 is countersunk due to the beveled surface 120 and mating profile of the fastener, although this is not required. This allows the head of the screw to be substantially flush with the upper housing. The head of the fastener is shown with a hex profile, but others may be used, such as square, slotted, Phillips, etc. Thus, the fastener 110 secures the upper housing 108 to the lower housing 106, and it is the juxtaposition of these two housing pieces that holds the cord 112 in place as desired. This avoids the problem in the prior art described above wherein the force of the set screw directly onto the cord will deleteriously pinch the cord, which can lead to undesired fraying or other damage to the cord.

Figure 9A:
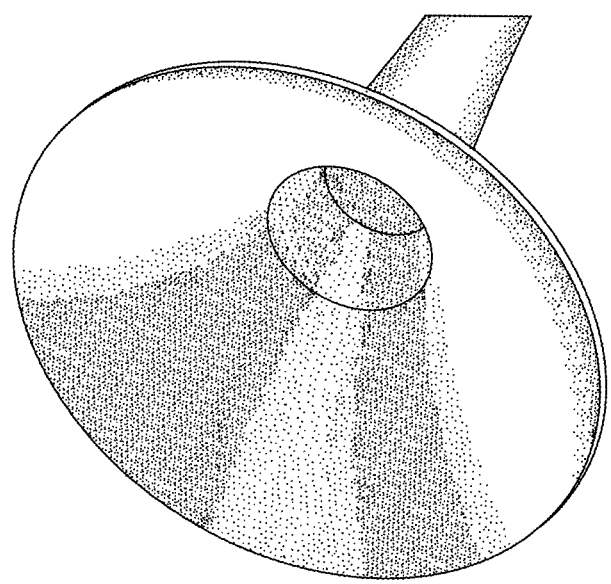
FIG. 9A is illustrative of the bell shape that is formed by the joining together of the flared surfaces.

The cord housing 105 is provided with a flared surface where the cord enters the housing. The flared surface enables the cord to bend and flex at the entry point without rubbing against a sharp corner edge as in the prior art. This advantageously provides flexibility of the cord without damage or fraying as in the prior art. The flared surfaces are also provided on the opposite side of the anchor device for maneuverability of the cord at the opposite entry point. FIG. 9A is illustrative of the shape that is formed by the joining together of the flared surfaces 114, 116. As can be seen, the flared surface area is similar to that of a bell horn in a trumpet or other brass instrument. Thus, the cradle of the lower housing has a first flared end portion 114, a middle portion 115, and a second flared end portion 116. Similarly, the clamp of the upper housing has a first flared end portion 117, a middle portion 118, and a second flared end portion 119, as shown in FIG. 2.

Figure 5:
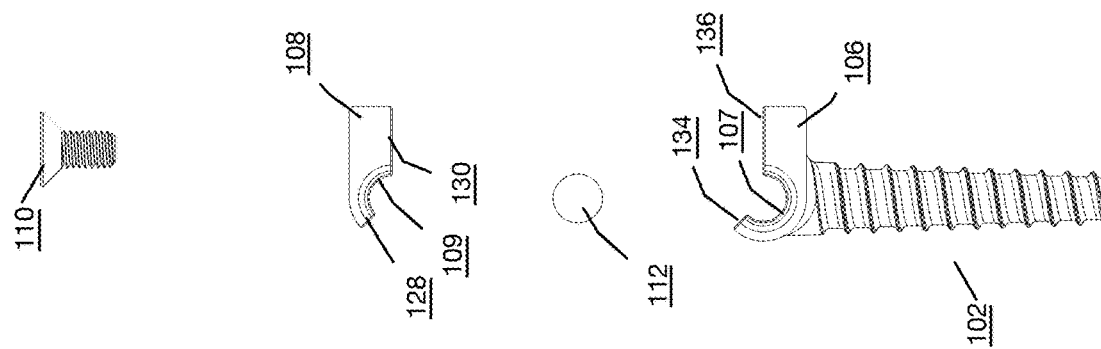
FIG. 5 is an exploded side view of the first embodiment of FIG. 1.
Figure 4:
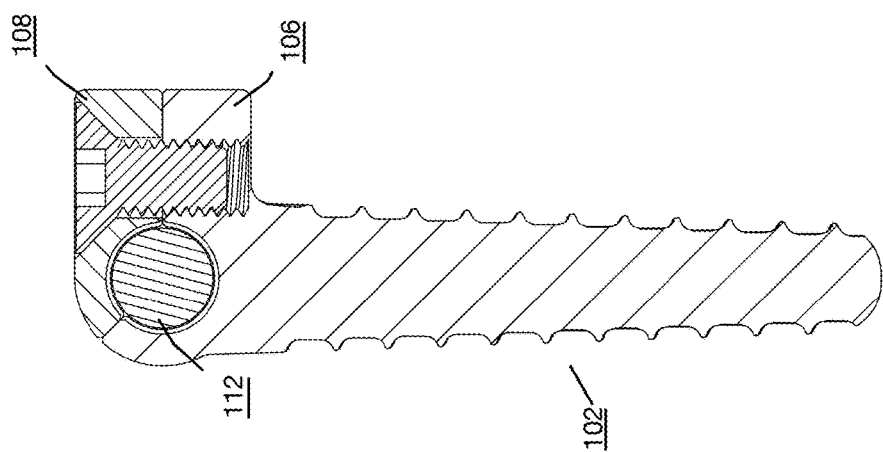
FIG. 4 is a side cross section view of the first embodiment of FIG. 1.
Figure 3:
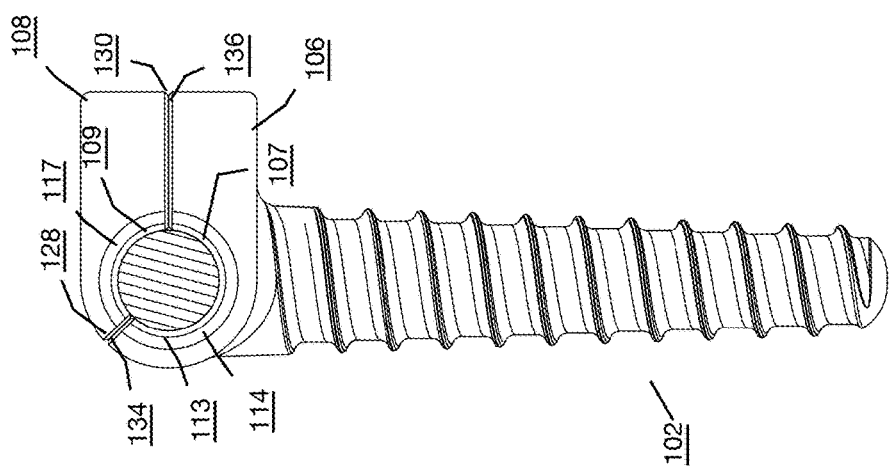
FIG. 3 is a side view of the first embodiment of FIG. 1.
Figure 6:
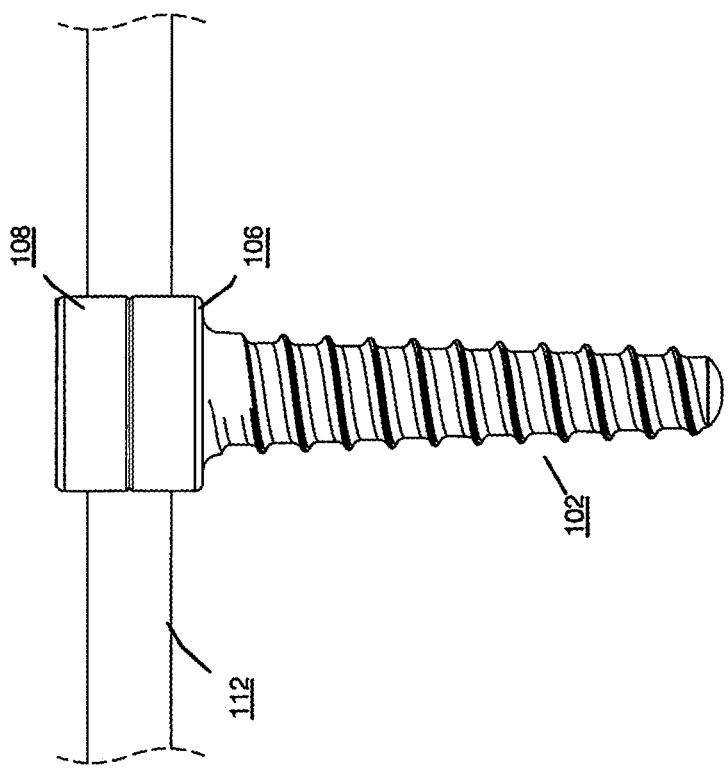
FIG. 6 is a rear view of the first embodiment of FIG. 1.
Figure 7:
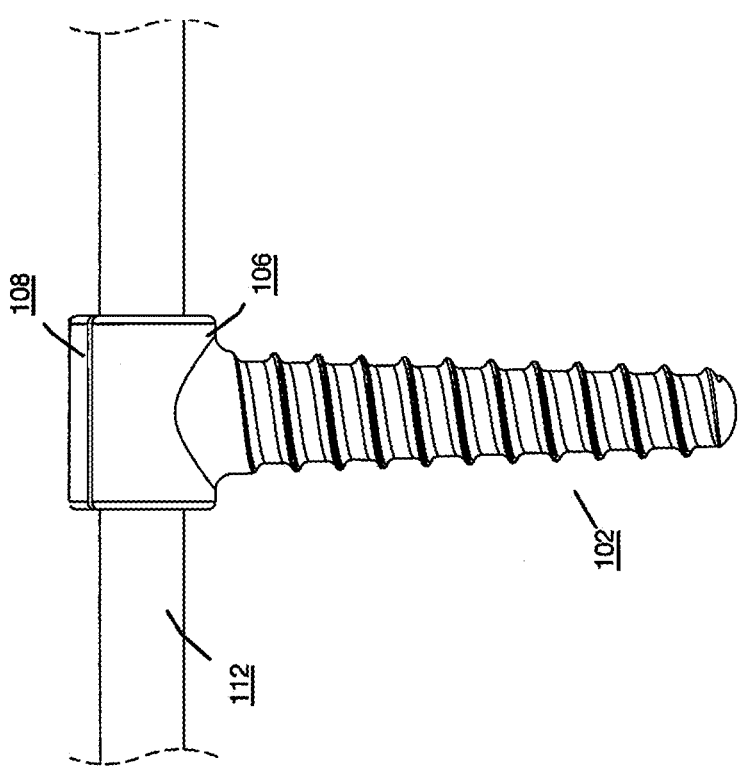
FIG. 7 is a front view of the first embodiment of FIG. 1.

With further reference to FIGS. 3, 4 and 5, it can be seen how the cord channel 113 is formed in a substantially cylindrical or circular fashion when the upper housing 108 is mated with the lower housing 106, which is suitable to encase the cord 112 therewithin. Here, the cradle 107 is partially cylindrical in that it provides a cross-sectional profile of greater than half of the cylinder and extends more than halfway around the cord, in particular approximately 225 degrees. Accordingly, the clamp 109 of the upper housing 108 is also partially cylindrical in that it provides a cross-sectional profile of less than half of the cylinder and extends less than halfway around the cord when placed over it, in particular approximately 135 degrees. As such, when the cord is placed into the lower housing 106 by the surgeon, it can be popped through (snapped in or press fit) with a small amount of force so the cord 112 temporarily compresses to fit within the cradle 107. In this manner, the cord is held in place temporarily by the cradle 107 until the surgeon locates the upper housing 108 in place with the clamp 109 over the cradle and secures it with the fastener 110. In the prior art, the opening in the lower portion is only 180 degrees and provides no ability to retain the cord in the place in this manner. The 225/135 degree pairings shown here are exemplary, and other opening placements and/or sizes may be used to accomplish the same temporary holding feature as described.

In the preferred embodiments described herein, a non-smooth or otherwise irregular surface is provided on the surface of the cradle middle portion 115 and the clamp middle portion 118 within the cord channel 113, imparting a locally compressive force on the cord, so that the cord is held securely in place when the upper housing 108 is joined to the lower housing 106 around the cord. Referring back to FIG. 2, in one embodiment, several ribs 121 are formed along the circumference of the cradle 107 of the lower housing 106, terminating in corresponding raised profiles 124 at the ends of each (see also FIG. 9). Likewise, several ribs 121 are formed along the length of the clamp 109 of the upper housing 108. These ribs help keep the cord in place within the housing 105 when assembled and prevents the cord from being pulled in either direction in the event there are stresses on the cord imparted during normal use. FIGS. 8A and 9 illustrate the location of the ribs and raised profiles 124 with respect to the cord 112 and how they compress the cord to hold it in place, wherein FIG. 8A is a top view of the anchor device with the cord pressed into the lower housing 106 and the upper housing not present and FIG. 9 is a top cross section view of the anchor device.

The number of ribs 121 running within the cord channel 113 may be varied from what is shown in the exemplary embodiment herein. In addition, the ribs on the clamp may be offset from those on the cradle, in the alternative to being aligned with each other as shown in the Figures. In another embodiment, a set of raised dimples or a roughened texture known as knurling are provided in place of the ribs as shown, in order to provide the desired traction along the cord. All of these variants may aid in distributing the forces imparted by the joining of the upper housing 108 with the lower housing 106 around and for securing the cord 112.

The lower housing 106 has a lower housing major surface 136, and the upper housing 108 similarly has an upper housing major surface 130. The upper housing major surface 130 substantially abuts the lower housing major surface 136 when the upper housing is joined to the lower housing and provides a stop to prevent overtightening of the upper housing to the lower housing. As shown in the preferred embodiment herein, the lower housing major surface and the upper housing major surface are flat and align with each other.

The lower housing 106 has a lower housing minor surface 134, and the upper housing 108 similarly has an upper housing minor surface 128. The upper housing minor surface 128 substantially abuts the lower housing minor surface 134 when the upper housing is joined to the lower housing and also provides a stop to prevent overtightening of the upper housing to the lower housing. As with the major surfaces in this preferred embodiment, the lower housing minor surface and the upper housing minor surface are flat and align with each other. Although the major and minor surfaces of both the upper housing and the lower housing are preferably flat, they may have other shapes that are designed to align and mate with each other, such as a V-shaped notch and mating protrusion.

The abutment of the upper housing minor surface to the lower housing minor surface also improves alignment of the upper housing and lower housing wherein the upper housing is prevented from rotating and spinning about an axis when the housings are adjoined together.

When the upper housing 108 is joined to the lower housing 106, the channel 113 is defined and holds the cord 112 as described above. In addition, the upper housing major flat surface 130 abuts against the lower housing major flat surface 136, and the upper housing minor flat surface 128 abuts against the lower housing minor flat surface 134. This enables better alignment of the opposing surfaces of the two housing portions since the fastener 110 is threaded into the aperture 122 offset from the channel 113, and the forces imparted by the tightened fastener are distributed along these flat surfaces rather than at a single point of contact, as in the prior art. This provides for a more robust hold on the cord than in the prior art. Additionally, this configuration provides a stop to prevent overtightening on the cord, which is not found in the prior art. This ensures that the forces imparted on the cord are consistent amongst the several anchor devices that are used in a given application, as well as being repeatable at various times and in various applications.

Another advantage of this embodiment is that the joining of the upper housing to the lower housing at the opposing major surfaces 130, 136 and at the opposing minor surfaces 128, 134 will cause a horizontal component of force and a vertical component of force along the x and y axes, respectively, that will compress the cord, thus ensuring a good compressive fit of the cord within the channel 113. Due to the shape of the channel 113, a substantially radially symmetrical compressive force is achieved. Provisional tightening of the cord through the fastener prior to final tightening is possible with this configuration of the invention.

The adjoining of the upper housing major surface to the lower housing major surface and the upper housing minor surface to the lower housing minor surface provides a limit to the compression of the cord by the clamp and the cradle.

As shown in the Figures, the fastener 110 is perpendicularly aligned with respect to the anchor device in a strictly vertical plane; however, it may be desired in some embodiments for the fastener to be inserted at an angle off of the y-axis in order to impart a partial horizontal component of force along the x-axis to aid in the joining together of the minor surfaces 128, 134, and/or to improve access during surgery (i.e., a better angle of attack for the fastening tool).

Additionally, the location of the fastener 110 with respect to the cord(s) held in place within the channel may differ from what is shown in the Figures; i.e., it may be more rearward or forward from what is shown (thus being diagonally located with respect to the cord channel). In another variant, the lower housing major surface may extend partially around or over the cord 112 such that the fastener 110 is located over the cord rather than being offset as shown.

The size of the channel 113 that holds the cord 112 is determined so that it will hold the cord snugly as the surfaces 128, 130, 134 and 136 are abutted together and held in place by the fastener 110. If the diameter of the cord 112 is too small, it will be loose within the channel 113 and not held in place properly. If the diameter of the cord is too large, the surfaces 128, 130, 134 and 136 will not be able to be joined to each other as described above (or too much force will be imparted onto the cord). Due to the compressibility of the cord, there is some tolerance on the appropriate diameter size. Thus, depending on variations in the characteristics of a cord or band being used (such as diameter/circumference, material used, and the like), differently sized anchor devices may be made available to a surgeon for optimal applications. For example, a typical cord may be 4 mm in diameter, but other diameters such as 5.2 mm may be used, in which case a differently sized anchor device under this invention may be required. Optionally, an anchor device may be designed to be suitable for a range of cords having different diameters and/or other characteristics.

FIGS. 10-18 illustrate a second major embodiment of this invention in which (at least) two cords are secured within the anchor device on a horizontal axis, and FIGS. 19-27 illustrate a third major embodiment of this invention in which (at least) two cords are secured within the anchor device on a vertical axis. These two embodiments share similar features with the first (single cord) embodiment described above but implement and elongated cylinder shaped cord channel to encase the pairs of cords.

Figure 11:
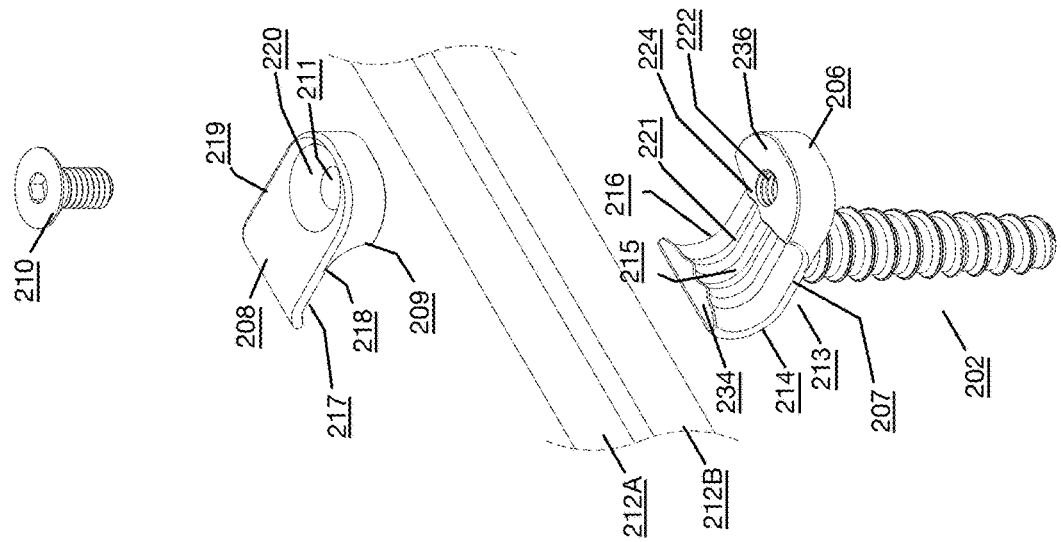
FIG. 11 is an exploded perspective view of the second embodiment of FIG. 10.
Figure 10:
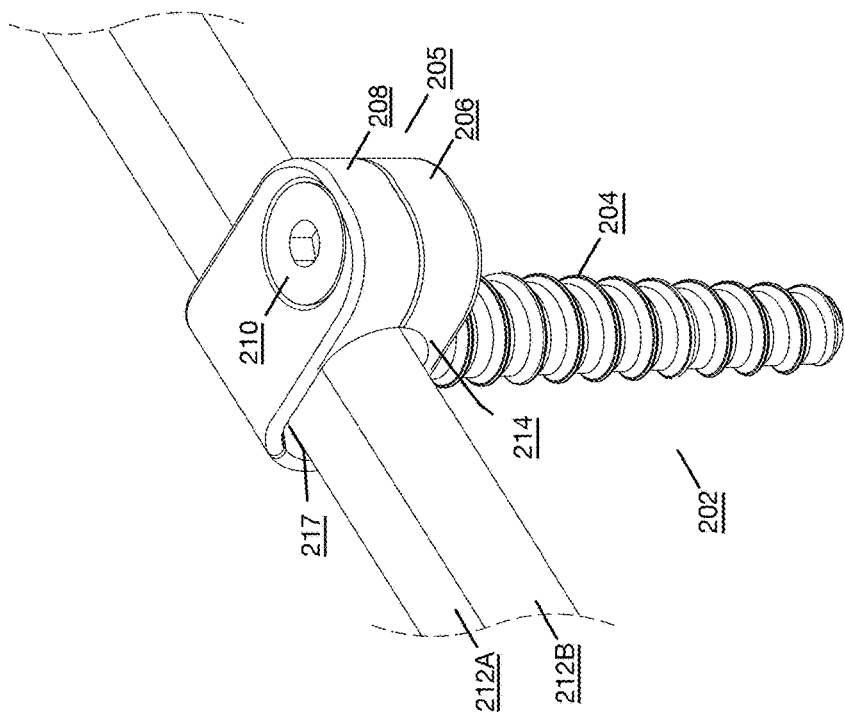
FIG. 10 is a perspective view of a second embodiment of the anchor device of the present invention suitable for double cords/bands that are horizontally offset from a center post.

Thus, with reference to FIGS. 10 and 11, the second embodiment of the anchor device, suitable for implementation with (at least) a pair of cords (or a single double width cord) on a horizontal axis, is shown. The anchor device 202 includes a threaded post 204 suitable for implantation into a bone as known in the art, and a cord housing 205 that is coupled to the post. The cord housing 205 maybe fixedly coupled to the post 204 as shown, so that the connection is rigid and unmoving, or the cord housing may be rotatably or otherwise movably coupled to the post. Shown in FIGS. 38 and 39 is a bone anchoring staple 450, as well known in the art, that may be utilized with the anchor device 202. The cord housing 205 is formed from two major components, i.e., a lower housing 206 and an upper housing 208. The lower housing 206 has a cradle 207 for receiving two cords, and the upper housing has a clamp 109 for placement over two cords 212A, 212B inserted into the cradle 207. In this multiple-cord embodiment, the cord channel formed by the clamp and the cradle is an elongated cylinder adapted to encase the cords side by side. In this case, the cradle provides a cross-sectional profile of greater than half of the elongated cylinder and the clamp provides a cross-sectional profile of less than half of the elongated cylinder. This enables the cords to be press fit into the cradle and held in place temporarily until the upper housing is joined to the lower housing.

Means for fastening the upper housing 208 to the lower housing 206 and securing the cords within the cord channel 213 may be, for example, a fastener 210. The fastener 210 in this second embodiment is a bolt, screw, or other type of device that can removably attach and fasten the upper housing to the lower housing. The threaded post 204 is inserted and threaded into the bone of the patient by the surgeon as known in the art, for example into a vertebra of a patient's spine during a procedure for correcting a scoliosis curve.

As with the first embodiment described above, the fastener 210 in the preferred embodiment of the present invention does not impinge directly and impart direct force upon the cord(s). Instead, the fastener 210 is inserted through an aperture 211 in the upper housing 208 and threaded into the threaded aperture 222 in the lower housing 206. The fastener 210 is then tightened as desired so that the upper housing 208 compresses against the cords 212A, 212B within the channel 213 in order to keep the cords clamped in and held snugly in place. As shown, the head of the fastener 210 is countersunk due to the beveled surface 220 and mating profile of the fastener, although this is not required. This allows the head of the screw to be substantially flush with the upper housing. The head of the fastener is shown with a hex profile, but others may be used, such as square, slotted, Phillips, etc. Thus, the fastener 210 secures the upper housing 208 to the lower housing 206, and it is the juxtaposition of these two housing pieces that holds the cords in place as desired. This avoids the problem in the prior art described above wherein the force of the set screw directly onto the cord will deleteriously pinch the cord, which can lead to undesired fraying or other damage to the cord.

The cord housing 205 is provided with a flared surface where the cords enters the housing. The flared surface enables the cord to each bend and flex at the entry point without rubbing against a sharp corner edge as in the prior art. This advantageously provides flexibility of the cords without damage or fraying as in the prior art. The flared surfaces are also provided on the opposite side of the anchor device for maneuverability of the cords at the opposite entry point. FIG. 9A is illustrative of the shape that is formed by the joining together of the flared surfaces 214, 216. As can be seen, the flared surface area is similar to that of a bell horn in a trumpet or other brass instrument. Thus, the cradle of the lower housing has a first flared end portion 214, a middle portion 215, and a second flared end portion 216. Similarly, the clamp of the upper housing has a first flared end portion 217, a middle portion 218, and a second flared end portion 219, as shown in FIG. 11.

Figure 14:
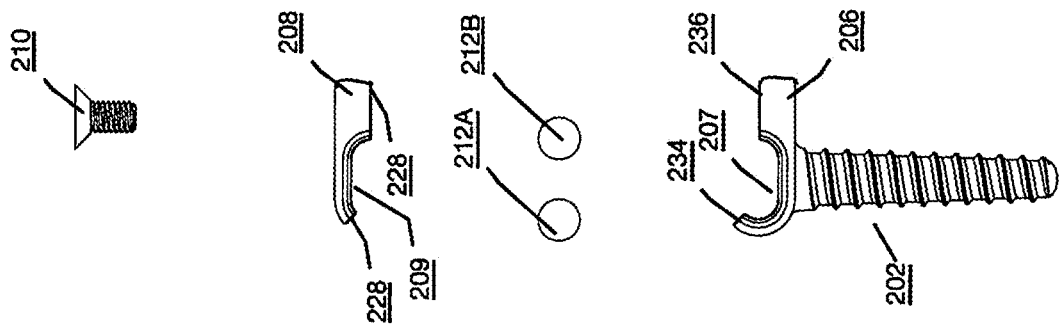
FIG. 14 is an exploded side view of the second embodiment of FIG. 10.
Figure 13:
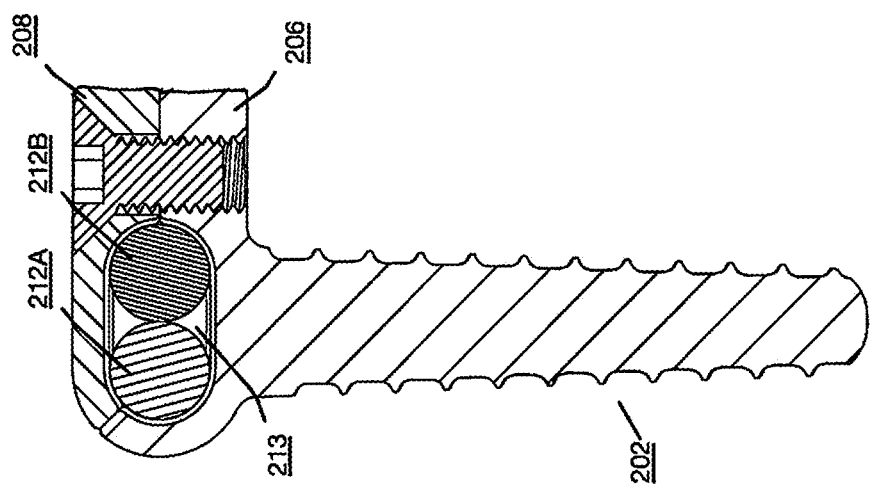
FIG. 13 is a side cross section view of the second embodiment of FIG. 10.
Figure 12:
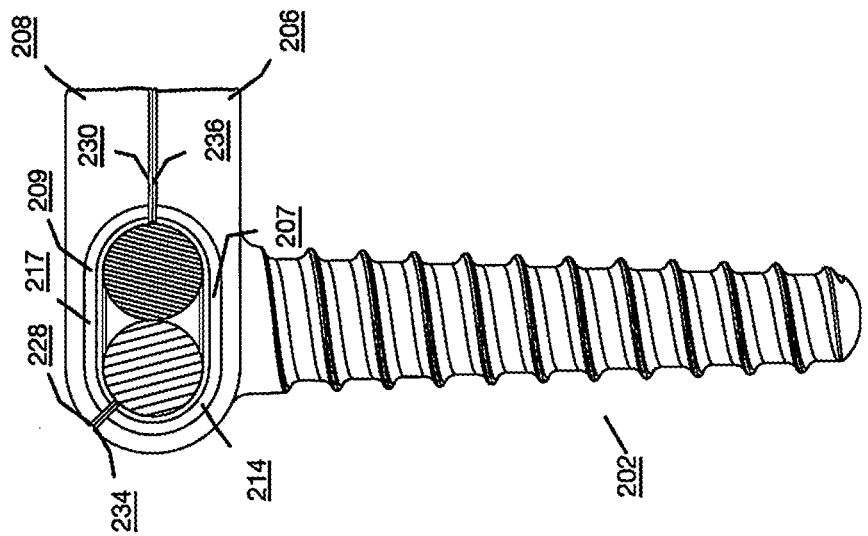
FIG. 12 is a side view of the second embodiment of FIG. 10.
Figure 16:
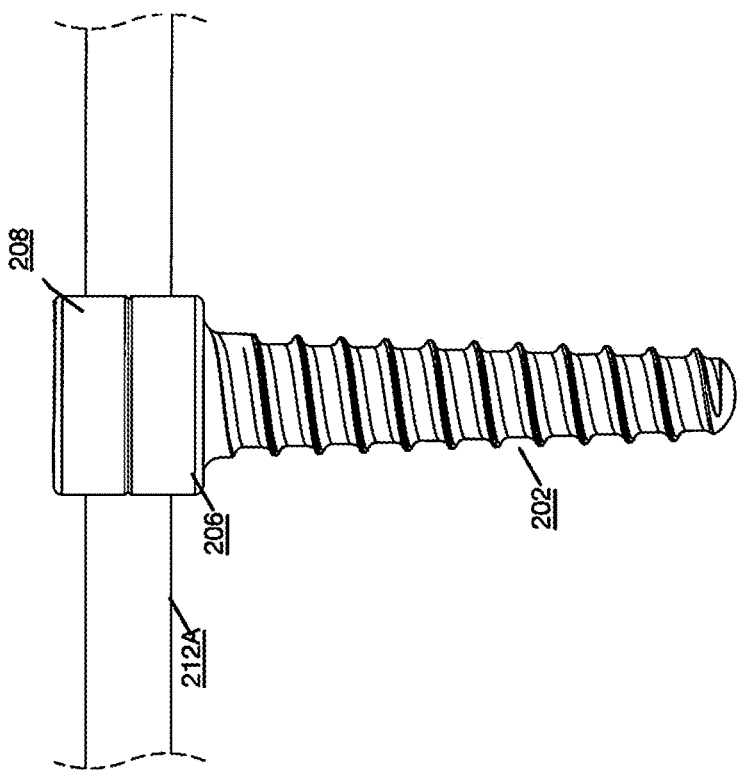
FIG. 16 is a front view of the second embodiment of FIG. 10.
Figure 15:
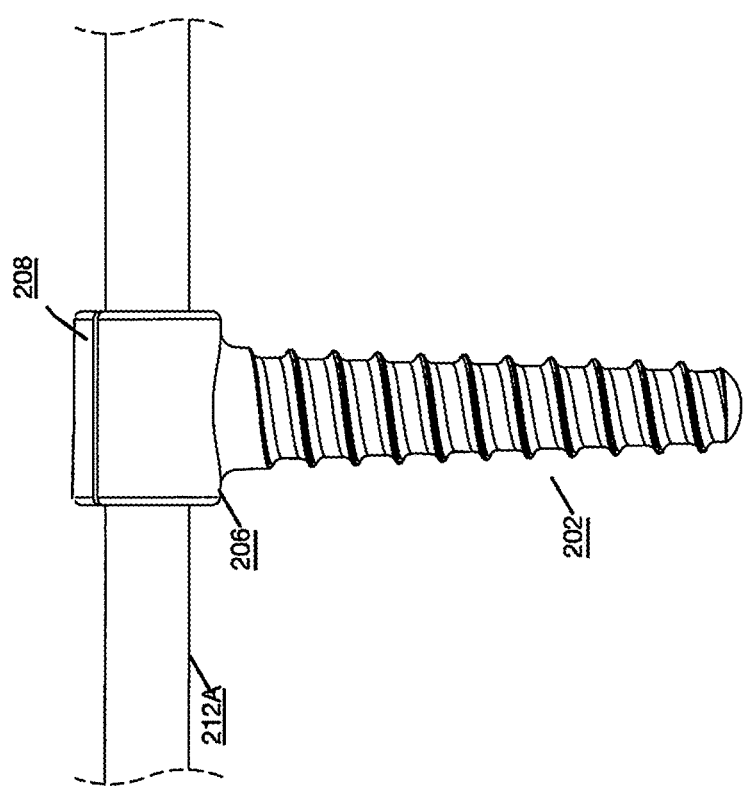
FIG. 15 is a rear view of the second embodiment of FIG. 10.

With further reference to FIGS. 12, 13 and 14, it can be seen how the cord channel 213 is formed as an elongated (oblong) cylinder when the upper housing 208 is mated with the lower housing 206, which is suitable to encase the cords 212A, 212B therewithin. Here, the cradle 207 provides a cross-sectional profile of greater than half of the elongated cylinder and the clamp provides a cross-sectional profile of less than half of the elongated cylinder. As such, when the cords are placed into the lower housing 206 by the surgeon, they are popped through (snapped in or press fit) with a small amount of force so the cords temporarily compress to fit within the cradle 207 (i.e., partially compressed and held in the cradle until the clamp is placed). In this manner, the cords are held in place temporarily by the cradle 207 until the surgeon locates the upper housing 208 in place with the clamp 209 over the cradle and secures it with the fastener 210.

Figure 18:
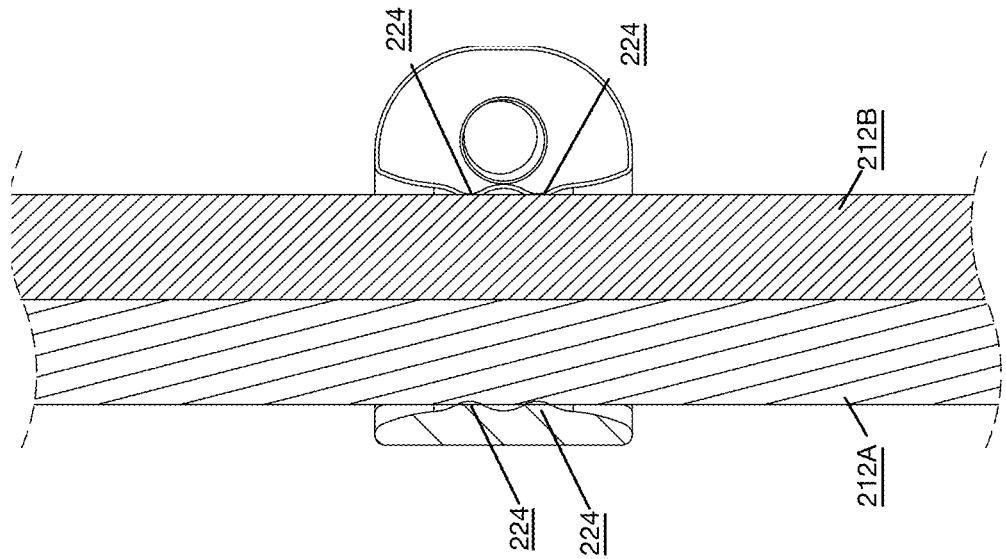
FIG. 18 is a top cross section view of the second embodiment of FIG. 10.
Figure 17:
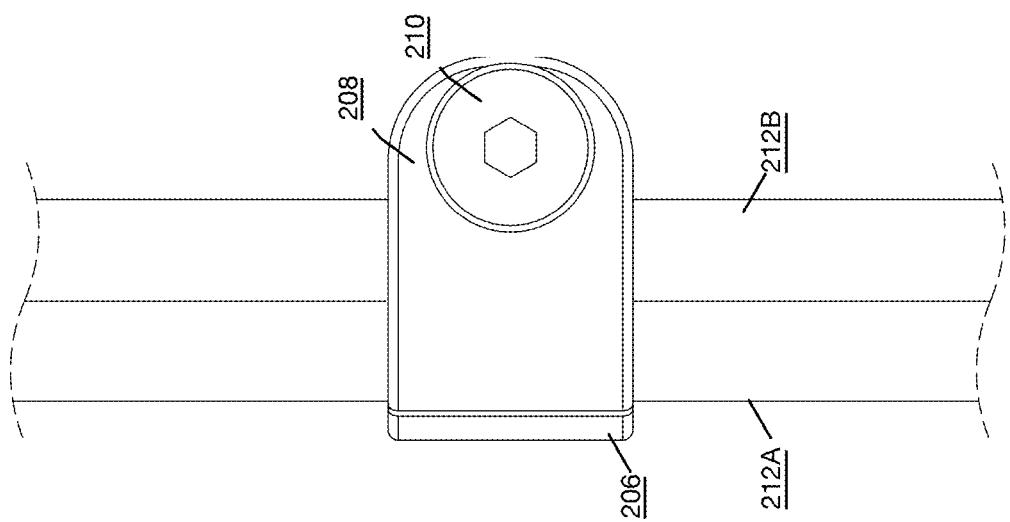
FIG. 17 is a top view of the second embodiment of FIG. 10.

In the preferred embodiments described herein, a non-smooth or otherwise irregular surface is provided on the surface of the cradle middle portion 215 and the clamp middle portion 218 within the cord channels 213, imparting a locally compressive force on the cord, so that the cords are held securely in place when the upper housing 208 is joined to the lower housing 206 around the cords. Referring back to FIG. 11, several ribs 221 are formed along the circumference of the cradle 207 of the lower housing 206, terminating in corresponding raised profiles 224 at the ends of each (see also FIG. 18). Likewise, several ribs 221 are formed along the length of the clamp 209 of the upper housing 208. These ribs help keep the cords in place within the housing 205 when assembled and prevents the cords from being pulled in either direction in the event there are stresses on the cords imparted during normal use. FIG. 18 illustrates the location of the ribs and raised profiles 224 with respect to the cords and how they compress the cords to hold them in place.

The number of ribs 221 running within the cord channel 213 may be varied from what is shown in the exemplary embodiment herein. In addition, the ribs on the clamp may be offset from those on the cradle, in the alternative to being aligned with each other as shown in the Figures. In another embodiment, a set of raised dimples or a roughened texture such as knurling are provided in place of the ribs as shown, in order to provide the desired traction along the cord. All of these variants may aid in distributing the forces imparted by the joining of the upper housing 208 with the lower housing 206 around and for securing the cords 212A, 212B.

The lower housing 206 has a lower housing major surface 236, and the upper housing 208 similarly has an upper housing major surface 230. The upper housing major surface 230 substantially abuts the lower housing major surface 236 when the upper housing is joined to the lower housing and provides a stop to prevent overtightening of the upper housing to the lower housing. As shown in the preferred embodiment herein, the lower housing major surface and the upper housing major surface are flat and align with each other.

The lower housing 206 has a lower housing minor surface 234, and the upper housing 208 similarly has an upper housing minor surface 228. The upper housing minor surface 228 substantially abuts the lower housing minor surface 234 when the upper housing is joined to the lower housing and also provides a stop to prevent overtightening of the upper housing to the lower housing. As with the major surfaces in this preferred embodiment, the lower housing minor surface and the upper housing minor surface are flat and align with each other. Although the major and minor surfaces of both the upper housing and the lower housing are preferably flat, they may have other shapes that are designed to align and mate with each other, such as a V-shaped notch and mating protrusion.

The abutment of the upper housing minor surface to the lower housing minor surface also improves alignment of the upper housing and lower housing wherein the upper housing is prevented from rotating and spinning about an axis when the housings are adjoined together.

When the upper housing 208 is joined to the lower housing 206, the channel 213 is defined and holds the cords as described above. In addition, the upper housing major flat surface 230 abuts against the lower housing major flat surface 236, and the upper housing minor flat surface 228 abuts against the lower housing minor flat surface 234. This enables better alignment of the opposing surfaces of the two housing portions since the fastener 210 is threaded into the aperture 222 offset from the channel 213, and the forces imparted by the tightened fastener are distributed along these flat surfaces rather than at a single point of contact, as in the prior art. This provides for a more robust hold on the cords than in the prior art. Additionally, this configuration provides a stop to prevent overtightening on the cords, which is not found in the prior art. This ensures that the forces imparted on the cords are consistent amongst the several anchor devices that are used in a given application, as well as being repeatable at various times and in various applications.

Another advantage of this embodiment is that the joining of the upper housing to the lower housing at the opposing major surfaces 230, 236 and at the opposing minor surfaces 228, 234 will cause a horizontal component of force and a vertical component of force along the x and y axes, respectively, that will compress the cords thus ensuring a good compressive fit of the cords within the channel 213. Due to the shape of the channel 213, a substantially radially symmetrical compressive force is achieved. Provisional tightening of the cord through the fastener prior to final tightening is possible with this configuration of the invention.

The adjoining of the upper housing major surface to the lower housing major surface and the upper housing minor surface to the lower housing minor surface provides a limit to the compression of the cords by the clamp and the cradle.

As shown in the Figures, the fastener 210 is perpendicularly aligned with respect to the anchor device in a strictly vertical plane; however, it may be desired in some embodiments for the fastener to be inserted at an angle off of the y-axis in order to impart a partial horizontal component of force along the x-axis to aid in the joining together of the minor surfaces 228, 234.

Figure 20:
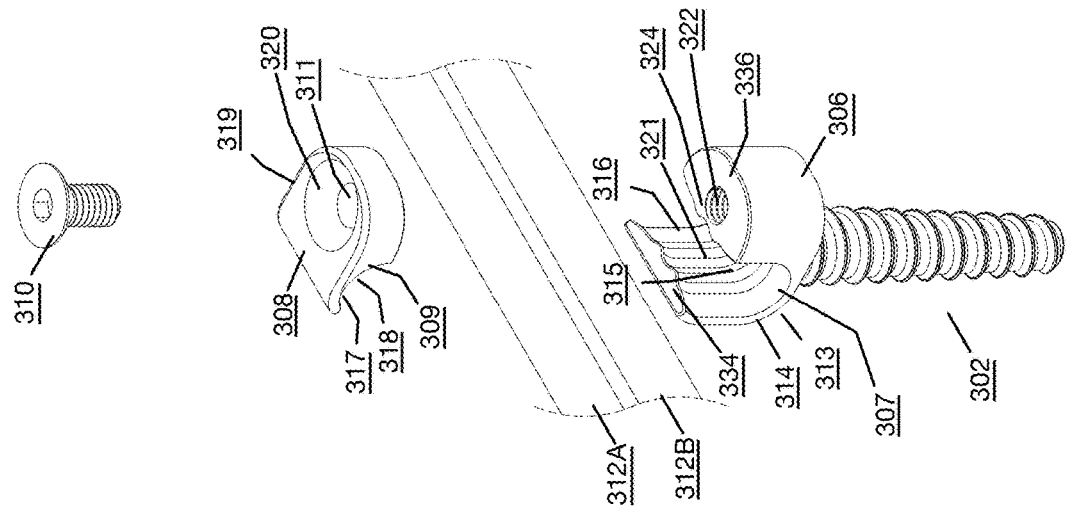
FIG. 20 is an exploded perspective view of the third embodiment of FIG. 19.
Figure 19:
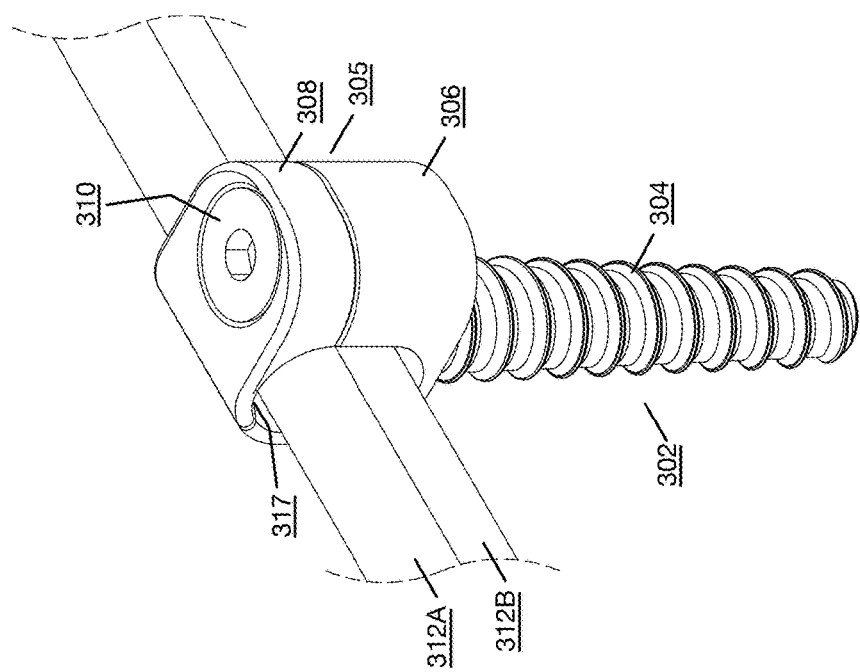
FIG. 19 is a perspective view of a third embodiment of the anchor device of the present invention suitable for double cords/bands that are vertically stacked.

Now, with reference to FIGS. 19 and 20, the third embodiment of the anchor device, suitable for implementation with (at least) a pair of cords (or a single double width cord) on a vertical axis, is shown. The anchor device 302 includes a threaded post 304 suitable for implantation into a bone as known in the art, and a cord housing 305 that is coupled to the post. The cord housing 305 maybe fixedly coupled to the post 304 as shown, so that the connection is rigid and unmoving, or the cord housing may be rotatably or otherwise movably coupled to the post. Shown in FIGS. 38 and 39 is a bone anchoring staple 450, as well known in the art, that may be utilized with the anchor device 302.

The cord housing 305 is formed from two major components, i.e., a lower housing 306 and an upper housing 308. The lower housing 306 has a cradle 307 for receiving two cords, and the upper housing has a clamp 309 for placement over two cords 312A, 312B inserted into the cradle 307. In this multiple-cord embodiment, the cord channel formed by the clamp and the cradle is an elongated cylinder adapted to encase the cords side by side (vertically). In this case, the cradle provides a cross-sectional profile of greater than half of the elongated cylinder and the clamp provides a cross-sectional profile of less than half of the elongated cylinder. This enables the cords to be press fit into the cradle and held in place temporarily until the upper housing is joined to the lower housing.

Means for fastening the upper housing 308 to the lower housing 306 and securing the cords within the cord channel 313 may be, for example, a fastener 310. The fastener 310 in this third embodiment is a bolt, screw, or other type of device that can removably attach and fasten the upper housing to the lower housing. The threaded post 304 is inserted and threaded into the bone of the patient by the surgeon as known in the art, for example into a vertebra of a patient's spine during a procedure for correcting a scoliosis curve.

As with the first embodiment described above, the fastener 310 in the preferred embodiment of the present invention does not impinge directly and impart direct force upon the cords. Instead, the fastener 310 is inserted through an aperture 311 in the upper housing 308 and threaded into the threaded aperture 322 in the lower housing 306. The fastener 310 is then tightened as desired so that the upper housing 208 compresses against the cords 312A, 312B within the channel 313 in order to keep the cords clamped in and held snugly in place. As shown, the head of the fastener 310 is countersunk due to the beveled surface 320 and mating profile of the fastener, although this is not required. This allows the head of the screw to be substantially flush with the upper housing. The head of the fastener is shown with a hex profile, but others may be used, such as square, slotted, Phillips, etc. Thus, the fastener 310 secures the upper housing 308 to the lower housing 306, and it is the juxtaposition of these two housing pieces that holds the cords in place as desired. This avoids the problem in the prior art described above wherein the force of the set screw directly onto the cord will deleteriously pinch the cord, which can lead to undesired fraying or other damage to the cord.

The cord housing 305 is provided with a flared surface where the cords enter the housing. The flared surface enables each cord to bend and flex at the entry point without rubbing against a sharp corner edge as in the prior art. This advantageously provides flexibility of the cords without damage or fraying as in the prior art. The flared surfaces are also provided on the opposite side of the anchor device for maneuverability of the cords at the opposite entry point. FIG. 9A is illustrative of the shape that is formed by the joining together of the flared surfaces 314, 316. As can be seen, the flared surface area is similar to that of a bell horn in a trumpet or other brass instrument. Thus, the cradle of the lower housing has a first flared end portion 314, a middle portion 315, and a second flared end portion 316. Similarly, the clamp of the upper housing has a first flared end portion 317, a middle portion 318, and a second flared end portion 319, as shown in FIG. 20.

Figure 23:
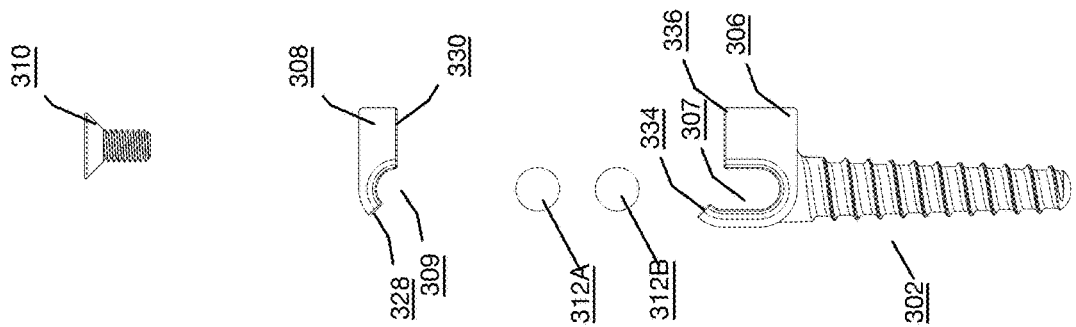
FIG. 23 is an exploded side view of the third embodiment of FIG. 19.
Figure 22:
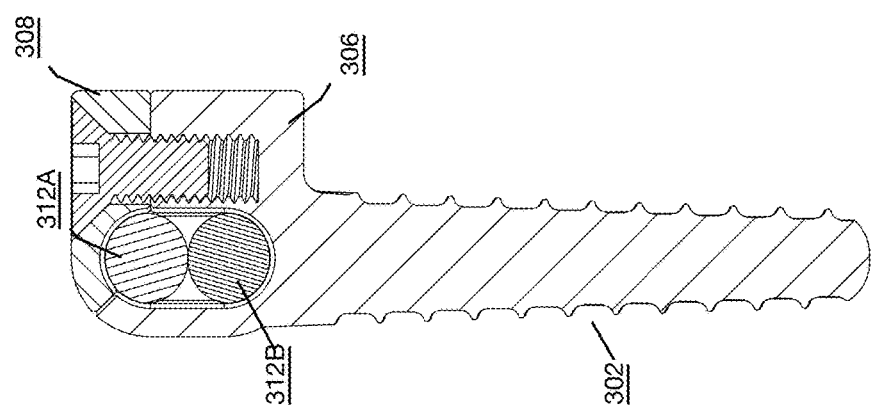
FIG. 22 is a side cross section view of the third embodiment of FIG. 19.
Figure 21:
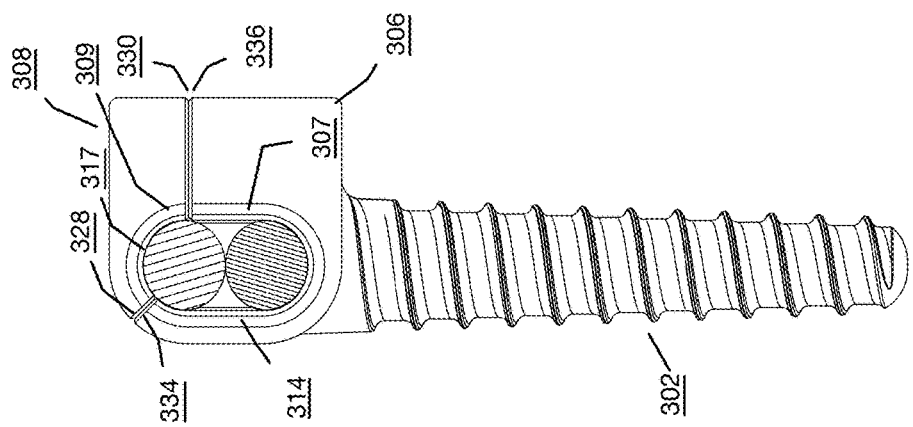
FIG. 21 is a side view of the third embodiment of FIG. 19.
Figure 25:
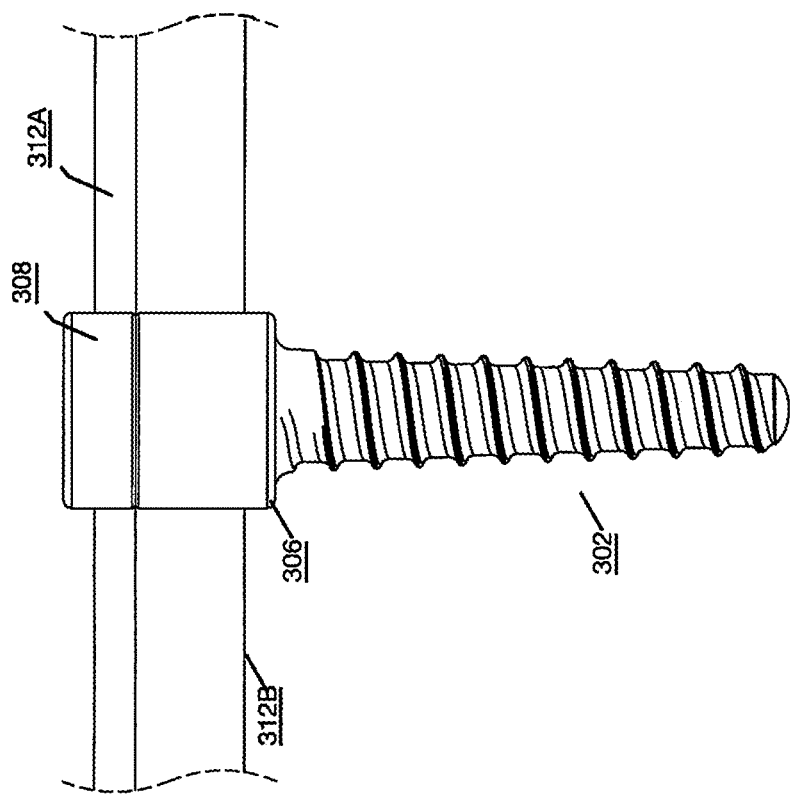
FIG. 25 is a front view of the third embodiment of FIG. 19.
Figure 24:
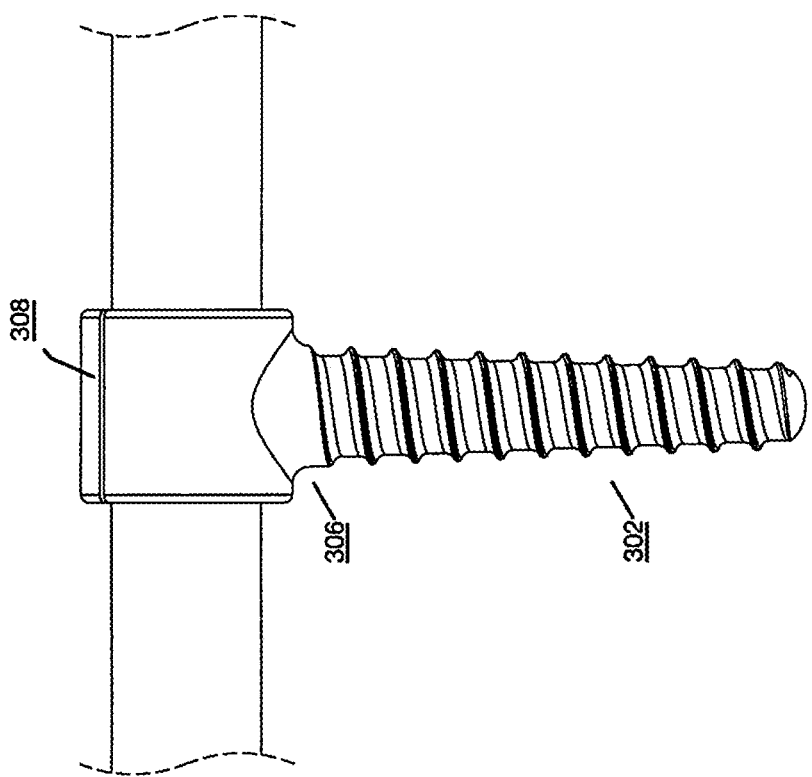
FIG. 24 is a rear view of the third embodiment of FIG. 19.

With further reference to FIGS. 21, 22 and 23, it can be seen how the cord channel 313 is formed as an elongated (oblong) cylinder when the upper housing 308 is mated with the lower housing 306, which is suitable to encase the cords 312A, 312B therewithin. Here, the cradle 307 provides a cross-sectional profile of greater than half of the elongated cylinder and the clamp provides a cross-sectional profile of less than half of the elongated cylinder. As such, when the cords are placed into the lower housing 306 by the surgeon, they are popped through (snapped in or press fit) with a small amount of force so the cords temporarily compress to fit within the cradle 307. In this manner, the cords are held in place temporarily by the cradle 307 until the surgeon locates the upper housing 308 in place with the clamp 309 over the cradle and secures it with the fastener 310.

Figure 27:
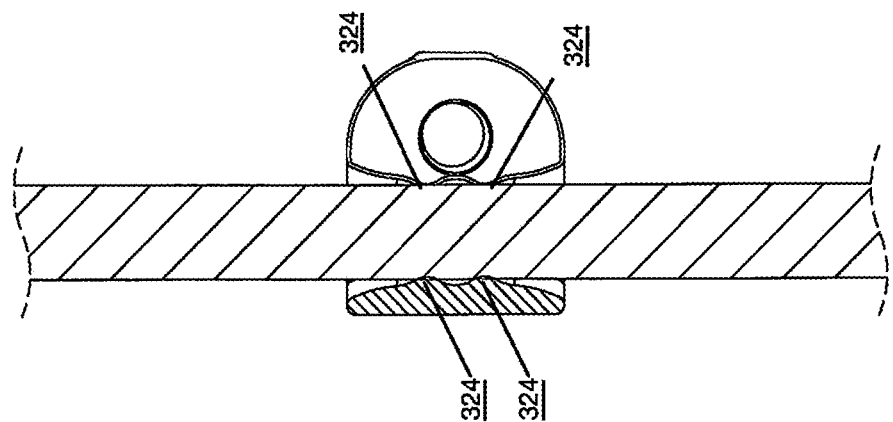
FIG. 27 is a top cross section view of the third embodiment of FIG. 19.
Figure 26:
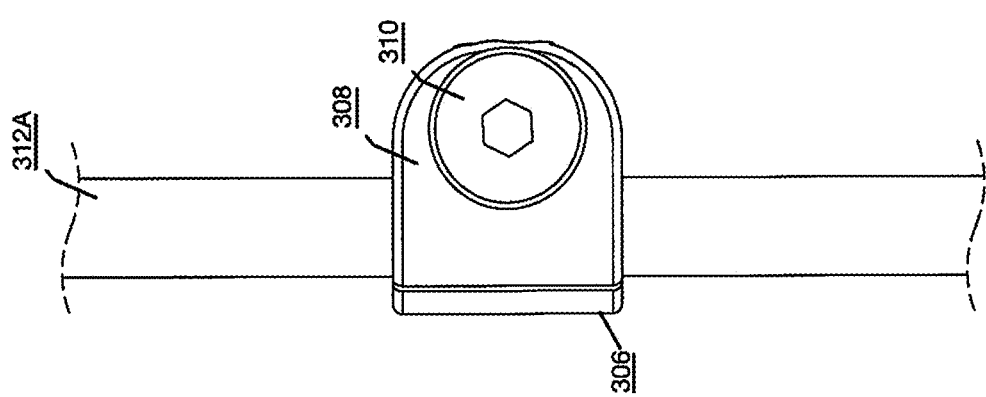
FIG. 26 is a top view of the third embodiment of FIG. 19.

In the preferred embodiments described herein, a non-smooth or otherwise irregular surface is provided on the surface of the cradle middle portion 315 and the clamp middle portion 318 within the cord channels 313, imparting a locally compressive force on the cord, so that the cords are held securely in place when the upper housing 308 is joined to the lower housing 306 around the cords. Referring back to FIG. 20, several ribs 321 are formed along the circumference of the cradle 307 of the lower housing 306, terminating in corresponding raised profiles 324 at the ends of each (see also FIG. 27). Likewise, several ribs 321 are formed along the length of the clamp 309 of the upper housing 308. These ribs help keep the cords in place within the housing 305 when assembled and prevents the cords from being pulled in either direction in the event there are stresses on the cords imparted during normal use. FIG. 27 illustrates the location of the ribs and raised profiles 324 with respect to the cords and how they compress the cords to hold them in place.

The number of ribs 321 running within the cord channel 313 may be varied from what is shown in the exemplary embodiment herein. In addition, the ribs on the clamp may be offset from those on the cradle, in the alternative to being aligned with each other as shown in the Figures. In another embodiment, a set of raised dimples or a roughened texture such as knurling are provided in place of the ribs as shown, in order to provide the desired traction along the cord. All of these variants may aid in distributing the forces imparted by the joining of the upper housing 308 with the lower housing 306 around and for securing the cords 312A, 312B.

The lower housing 306 has a lower housing major surface 336, and the upper housing 308 similarly has an upper housing major surface 330. The upper housing major surface 330 substantially abuts the lower housing major surface 336 when the upper housing is joined to the lower housing and provides a stop to prevent overtightening of the upper housing to the lower housing. As shown in the preferred embodiment herein, the lower housing major surface and the upper housing major surface are flat and align with each other.

The lower housing 306 has a lower housing minor surface 334, and the upper housing 308 similarly has an upper housing minor surface 328. The upper housing minor surface 328 substantially abuts the lower housing minor surface 334 when the upper housing is joined to the lower housing and also provides a stop to prevent overtightening of the upper housing to the lower housing. As with the major surfaces in this preferred embodiment, the lower housing minor surface and the upper housing minor surface are flat and align with each other. Although the major and minor surfaces of both the upper housing and the lower housing are preferably flat, they may have other shapes that are designed to align and mate with each other, such as a V-shaped notch and mating protrusion.

The abutment of the upper housing minor surface to the lower housing minor surface also improves alignment of the upper housing and lower housing wherein the upper housing is prevented from rotating and spinning about an axis when the housings are adjoined together.

When the upper housing 308 is joined to the lower housing 306, the channel 313 is defined and holds the cords as described above. In addition, the upper housing major flat surface 330 abuts against the lower housing major flat surface 336, and the upper housing minor flat surface 328 abuts against the lower housing minor flat surface 334. This enables better alignment of the opposing surfaces of the two housing portions since the fastener 310 is threaded into the aperture 322 offset from the channel 313, and the forces imparted by the tightened fastener are distributed along these flat surfaces rather than at a single point of contact, as in the prior art. This provides for a more robust hold on the cords than in the prior art. Additionally, this configuration provides a stop to prevent overtightening on the cords, which is not found in the prior art. This ensures that the forces imparted on the cords are consistent amongst the several anchor devices that are used in a given application, as well as being repeatable at various times and in various applications.

Another advantage of this embodiment is that the joining of the upper housing to the lower housing at the opposing major surfaces 330, 336 and at the opposing minor surfaces 328, 334 will cause a horizontal component of force and a vertical component of force along the x and y axes, respectively, that will compress the cords thus ensuring a good compressive fit of the cords within the channel 313. Due to the shape of the channel 313, a substantially radially symmetrical compressive force is achieved. Provisional tightening of the cord through the fastener prior to final tightening is possible with this configuration of the invention.

The adjoining of the upper housing major surface to the lower housing major surface and the upper housing minor surface to the lower housing minor surface provides a limit to the compression of the cords by the clamp and the cradle.

As shown in the Figures, the fastener 310 is perpendicularly aligned with respect to the anchor device in a strictly vertical plane; however, it may be desired in some embodiments for the fastener to be inserted at an angle off of the y-axis in order to impart a partial horizontal component of force along the x-axis to aid in the joining together of the minor surfaces 328, 334.

A fourth embodiment of the invention, also suitable for encasing multiple cords, is shown in FIGS. 28-37. This embodiment differs from the second and third multi-cord embodiments described above in that a pair of cord channels are provided, each of which is suitable for encasing and securing at least one cord, rather than the single channel design of the above embodiments.

Figure 29:
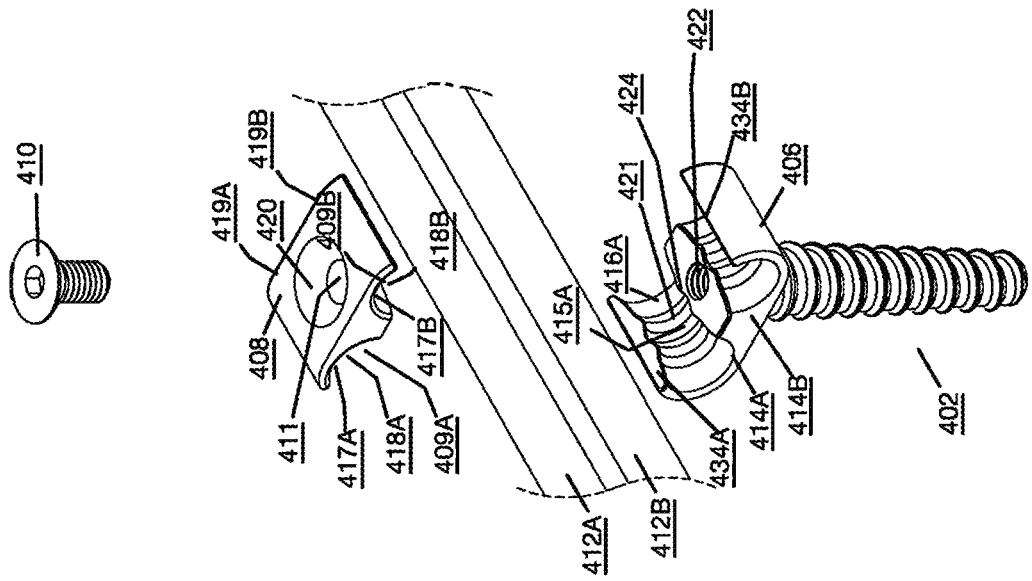
FIG. 29 is an exploded perspective view of the fourth embodiment of FIG. 28.
Figure 28:
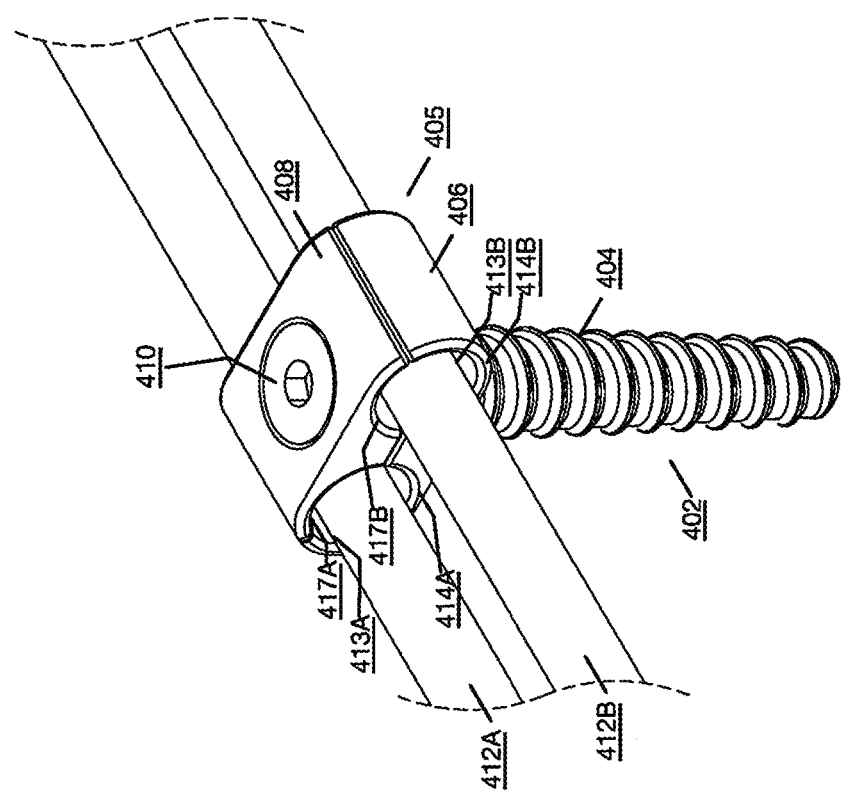
FIG. 28 is a perspective view of a fourth embodiment of the anchor device of the present invention suitable for double cords/bands that are horizontally centered over a center post.

Thus, with reference to FIGS. 28 and 29, the fourth embodiment of the anchor device, suitable for implementation with (at least) a pair of cords on a horizontal axis, is shown. The anchor device 402 includes a threaded post 404 suitable for implantation into a bone as known in the art, and a cord housing 405 that is coupled to the post. The cord housing 405 maybe fixedly coupled to the post 404 as shown, so that the connection is rigid and unmoving, or the cord housing may be rotatably or otherwise movably coupled to the post. Shown in FIGS. 38 and 39 is a bone anchoring staple 450, as well known in the art, that may be utilized with the anchor device 402.

The cord housing 405 is formed from two major components, i.e., a lower housing 406 and an upper housing 408. The lower housing 406 has a pair of cradles 407A, 407B (see FIG. 32), each for receiving one of the two cords 412A, 412B, and the upper housing has a pair of clamps 409A, 409B for placement over the two cords inserted into the cradles. In this multiple-cord embodiment, the cord channels 413A, 413B formed by the clamps 409A, 409B and the cradles 407A, 407B are each substantially cylindrical.

In this embodiment, each cradle 407A, 407B provides a cross-sectional profile of greater than half of the cylinder and the associated clamp provides a cross-sectional profile of less than half of the cylinder, so that each cord 412A, 412B may be press fit into the associated cradle 407A, 407B and held in place temporarily until the upper housing 408 is joined to the lower housing 406.

Means for fastening the upper housing 408 to the lower housing 406 and securing the cords within the cord channels 413A, 413B may be, for example, a fastener 410. The fastener 410 in this embodiment is a bolt, screw, or other type of device that can removably attach and fasten the upper housing to the lower housing. The threaded post 404 is inserted and threaded into the bone of the patient by the surgeon as known in the art, for example into a vertebra of a patient's spine during a procedure for correcting a scoliosis curve.

As with the embodiments described above, the fastener 410 does not impinge directly and impart direct force upon the cords. Instead, the fastener 410 is inserted through an aperture 411 in the upper housing 408 and threaded into the threaded aperture 422 in the lower housing 406. The fastener 410 is then tightened as desired so that the upper housing 408 compresses against the cords 412A, 412B within the respective channels 413A, 413B in order to keep the cords clamped in and held snugly in place. As shown, the head of the fastener 410 is countersunk due to the beveled surface 420 and mating profile of the fastener, although this is not required. This allows the head of the screw to be substantially flush with the upper housing. The head of the fastener is shown with a hex profile, but others may be used, such as square, slotted, Phillips, etc. Thus, the fastener 410 secures the upper housing 408 to the lower housing 406, and it is the juxtaposition of these two housing pieces that holds the cords in place as desired. This avoids the problem in the prior art described above wherein the force of the set screw directly onto the cord will deleteriously pinch the cord, which can lead to undesired fraying or other damage to the cord.

In this fourth embodiment, the fastener is located between the pair of cord channels 413A, 413B as shown in the various Figures, thus imparting a symmetrically distributed force onto each clamp when the upper housing is joined to the lower housing to encase the cords.

The cord housing 405 is provided with a flared surface where each cord enters the housing in the respective cord channel 413A, 413B. Each flared surface enables the associated cord to bend and flex at the entry point without rubbing against a sharp corner edge as in the prior art. This advantageously provides flexibility of the cords without damage or fraying as in the prior art. The flared surfaces are also provided on the opposite side of the anchor device for maneuverability of the cords at the opposite entry point. FIG. 9A is illustrative of the shape that is formed by the joining together of the flared surfaces. As can be seen, the flared surface area is similar to that of a bell horn in a trumpet or other brass instrument. Thus, cradle 407A of the lower housing 406 has a first flared end portion 414A, a middle portion 415A, and a second flared end portion 416A; and cradle 407B of the lower housing 406 has a first flared end portion 414B, a middle portion 415B, and a second flared end portion 416B. Similarly, each clamp of the upper housing has first flared end portions 417A, 417B, middle portions 418A, 418B, and second flared end portions 419A, 419B, as shown in FIG. 29.

Figure 32:
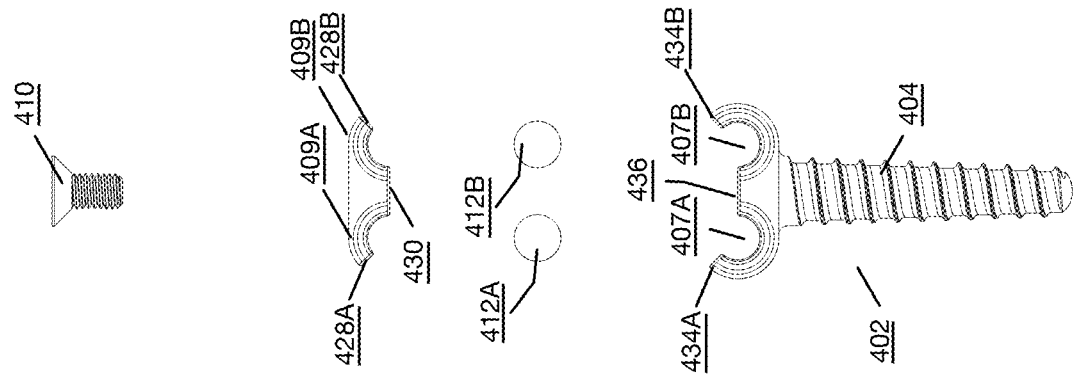
FIG. 32 is an exploded side view of the fourth embodiment of FIG. 28.
Figure 31:
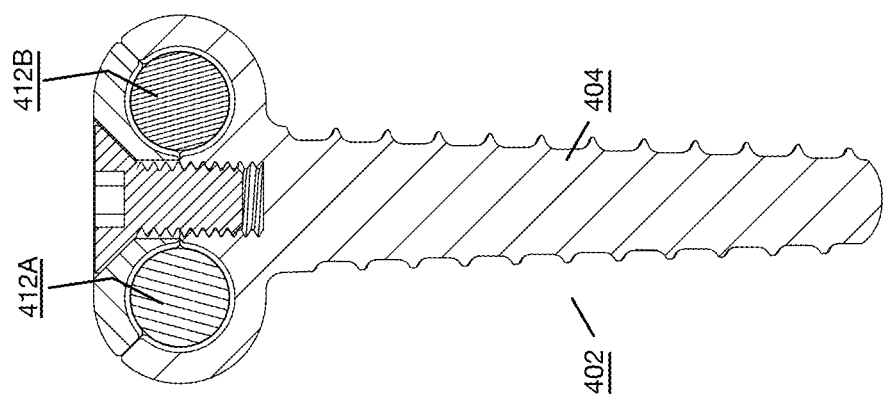
FIG. 31 is a side cross section view of the fourth embodiment of FIG. 28.
Figure 30:
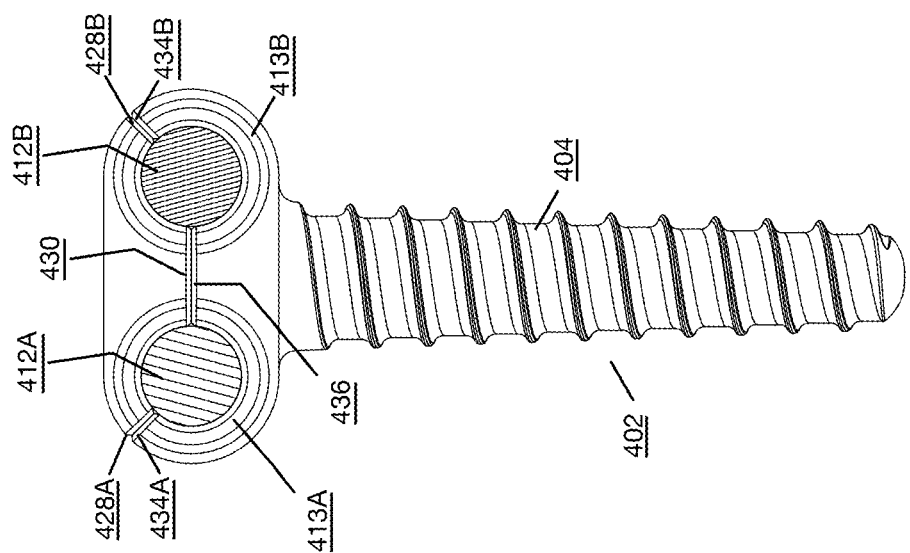
FIG. 30 is a side view of the fourth embodiment of FIG. 28.

With further reference to FIGS. 30, 31 and 32, it can be seen how the cord channels 413A, 413B are each formed in a substantially cylindrical or circular fashion when the upper housing 408 is mated with the lower housing 406, which is suitable to encase the cords 412A, 412B therewithin. Here, each cradle 407A, 407B is partially cylindrical in that each provides a cross-sectional profile of greater than half of a cylinder and extends more than halfway around each cord, in particular approximately 225 degrees. Accordingly, each clamp 409A, 409B of the upper housing 408 is also partially cylindrical in that each provides a cross-sectional profile of less than half of the cylinder and extends less than halfway around each cord when placed over them, in particular approximately 135 degrees. As such, when the cords are placed into the lower housing 406 by the surgeon, they are popped through (snapped in or press fit) with a small amount of force so the cords temporarily compress to fit within each cradle. In this manner, the cords are held in place temporarily by each cradle until the surgeon locates the upper housing 408 in place with the clamps over the respective cradle and secures it with the fastener 410.

Figure 35:
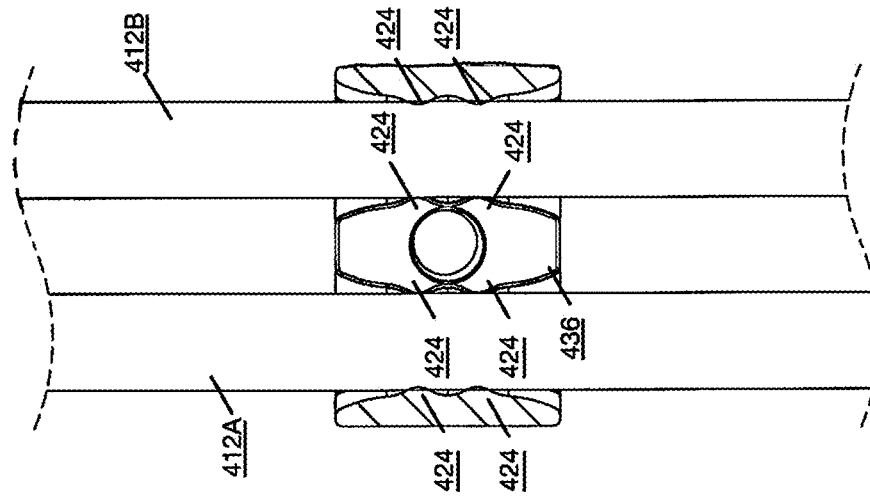
FIG. 35 is a top cross section view of the fourth embodiment of FIG. 28.
Figure 34:
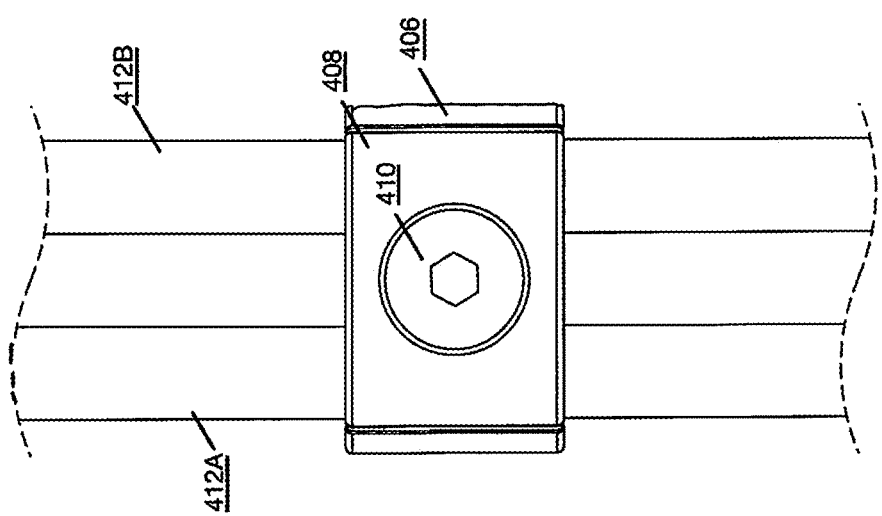
FIG. 34 is a top view of the fourth embodiment of FIG. 28.

In the preferred embodiments described herein, a non-smooth or otherwise irregular surface is provided on the surface of each lower housing middle portion 415A, 415B and each upper housing middle portion 418A, 418B within the cord channels 413A, 413B, imparting a locally compressive force on the cords, so that the cords are held securely in place when the upper housing 408 is joined to the lower housing 406 around the cords. Referring back to FIG. 29, several ribs 421 are formed along the circumference of each cradle 407A, 407B of the lower housing 406, terminating in corresponding raised profiles 424 at the ends of each (see also FIG. 35). Likewise, several ribs 421 are formed along the length of each clamp 409A, 409B of the upper housing 408. These ribs help keep the cords in place within the housing 405 when assembled and prevents the cords from being pulled in either direction in the event there are stresses on the cords imparted during normal use. FIG. 35 illustrates the location of the ribs and raised profiles 424 with respect to the cords and how they compress the cords to hold them in place.

The number of ribs 421 running within each cord channel 413A, 413B may be varied from what is shown in the exemplary embodiment herein. In addition, the ribs on the clamps may be offset from those on the cradles, in the alternative to being aligned with each other as shown in the Figures. In another embodiment, a set of raised dimples or a roughened texture such as knurling are provided in place of the ribs as shown, in order to provide the desired traction along the cord. All of these variants may aid in distributing the forces imparted by the joining of the upper housing 408 with the lower housing 406 around and for securing the cords 412A, 412B.

The lower housing 406 has a lower housing major surface 436, and the upper housing 408 similarly has an upper housing major surface 430. The upper housing major surface 430 substantially abuts the lower housing major surface 436 when the upper housing is joined to the lower housing and provides a stop to prevent overtightening of the upper housing to the lower housing. As shown in the preferred embodiment herein, the lower housing major surface and the upper housing major surface are flat and align with each other.

The lower housing 406 has a pair of lower housing minor surfaces 434A, 434B, and the upper housing 408 similarly has a pair of upper housing minor surfaces 428A, 428B. Each of the upper housing minor surfaces substantially abut the opposing respective lower housing minor surface when the upper housing is joined to the lower housing and also provides a stop to prevent overtightening of the upper housing to the lower housing. As with the major surfaces in this preferred embodiment, the lower housing minor surfaces and the upper housing minor surfaces are flat and align with each other. Although the major and minor surfaces of both the upper housing and the lower housing are preferably flat, they may have other shapes that are designed to align and mate with each other, such as a V-shaped notch and mating protrusion.

The abutment of the upper housing minor surfaces 428A, 428B to the lower housing minor surfaces 434A, 434B also improves alignment of the upper housing and lower housing wherein the upper housing is prevented from rotating and spinning about an axis when the housings are adjoined together.

When the upper housing 408 is joined to the lower housing 406, each cord channel 413A, 413B is defined and holds the cords as described above. In addition, the upper housing major flat surface 430 abuts against the lower housing major flat surface 436, and the upper housing minor flat surfaces 428A, 428B each abut against the opposing respective lower housing minor flat surfaces 434A, 434B.

This enables better alignment of the opposing surfaces of the two housing portions since the fastener 410 is threaded into the aperture 422 between the channels 413A, 413B, and the forces imparted by the tightened fastener are distributed along these flat surfaces rather than at a single point of contact, as in the prior art. This provides for a more robust hold on the cords than in the prior art. Additionally, this configuration provides a stop to prevent overtightening on the cords, which is not found in the prior art. This ensures that the forces imparted on the cords are consistent amongst the several anchor devices that are used in a given application, as well as being repeatable at various times and in various applications.

Another advantage of this embodiment is that the joining of the upper housing to the lower housing at the opposing major surfaces and at the opposing minor surfaces will cause a horizontal component of force and a vertical component of force along the x and y axes, respectively, that will compress the cords thus ensuring a good compressive fit of the cords within the channels. Due to the shape of each channel, a substantially radially symmetrical compressive force is achieved. Provisional tightening of the cord through the fastener prior to final tightening is possible with this configuration of the invention.

The adjoining of the upper housing major surface to the lower housing major surface and the upper housing minor surfaces to the lower housing minor surfaces provide a limit to the compression of the cords by the clamps and the cradles.

As shown in the Figures, the fastener 410 is aligned perpendicularly with respect to the anchor device in a vertical plane; however, it may be desired in some embodiments for the fastener to be inserted at an angle off of the y-axis in order to impart a partial horizontal component of force along the x-axis to aid in the joining together of the various surfaces.

Figure 36:
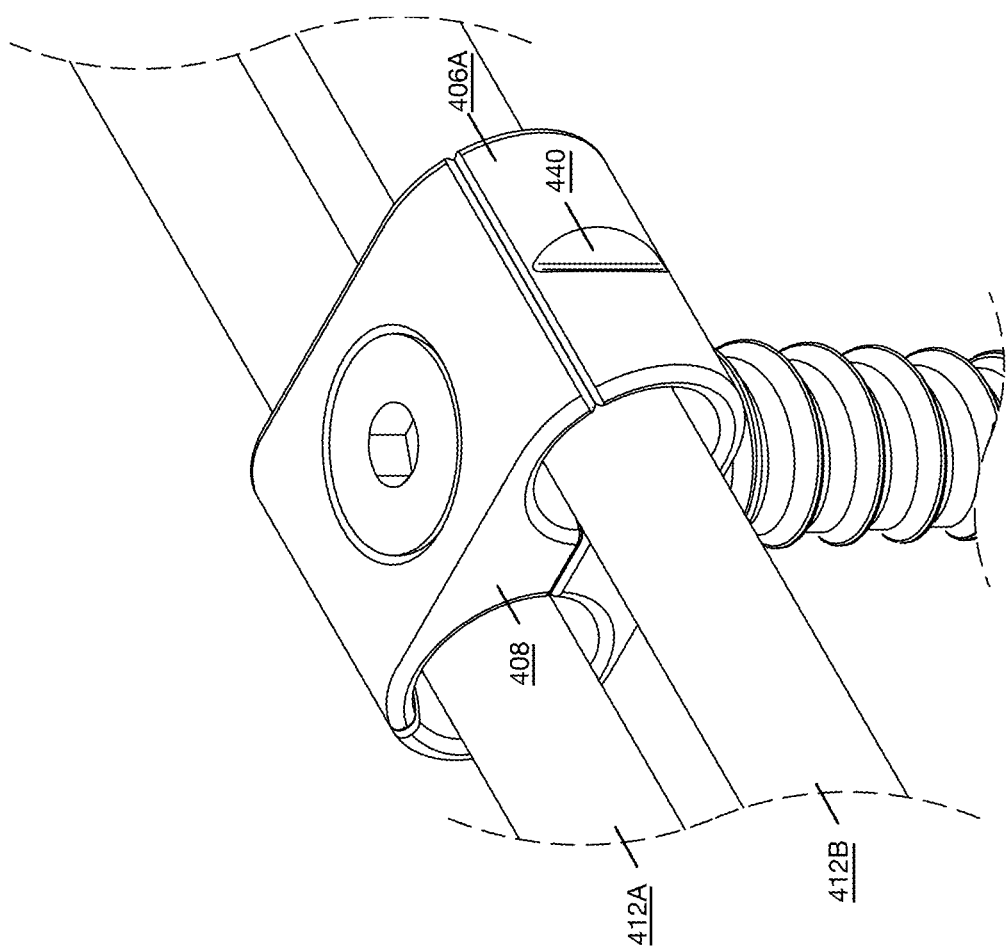
FIG. 36 is a perspective view of a modification to the fourth embodiment of the invention.
Figure 37:
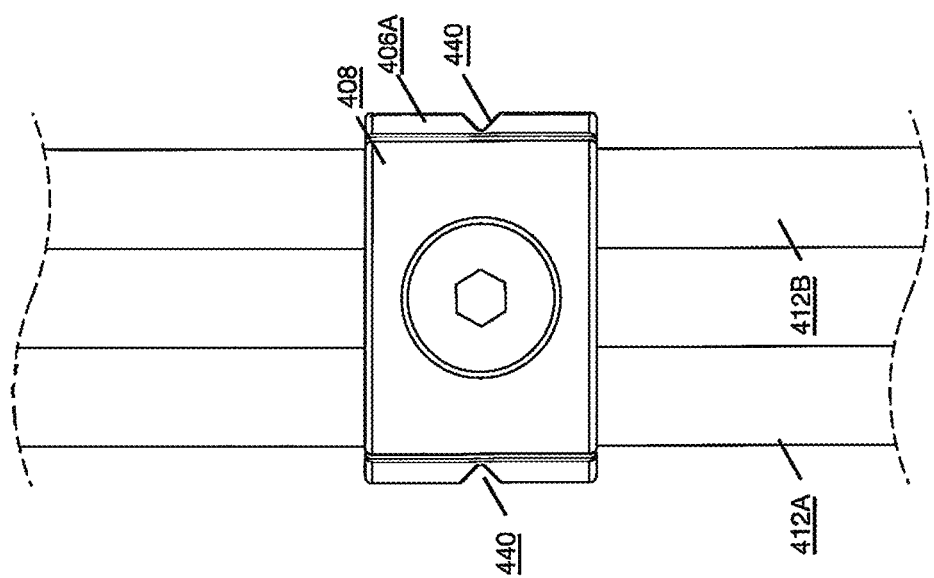
FIG. 37 is a top view of the modified fourth embodiment of FIG. 36.

FIG. 36 is a perspective view of a modification to the fourth embodiment of the invention, and FIG. 37 is a top view of the modified fourth embodiment of FIG. 36. Shown is a modified lower housing 406A, into which a V-shaped notch 440 is provided on either or both sides of the housing as shown. A leveraging tool (not shown) may be used in conjunction with the notch(es) 440 to give the surgeon better leverage and control when placing the anchor device into the bone of the patient. In addition, this enables more secure fixation when leveraging the anchor device after implantation, to manipulate the vertebral bodies (just prior to tightening the cords). This feature may also be used with any of the three prior embodiments described herein.

We claim:

1. An anchor device for insertion into a bone, comprising
a post suitable for implantation into a bone, and
a cord housing coupled to the post, comprising
a lower housing comprising a cradle for receiving therein at least one cord; and
an upper housing comprising a clamp for placement over the at least one cord inserted into the cradle;
wherein the joining of the upper housing to the lower housing forms a cord channel by the cradle and the clamp, to encase the at least one cord placed into the cradle; and
means for fastening the upper housing to the lower housing and securing the at least one cord within the cord channel;
wherein
the cradle comprises a first end portion where the cord enters the cord channel, a middle portion, and a second end portion where the cord exits the cord channel, wherein the first end portion and the second end portion each comprise an outwardly flared surface along an axis defined by the cord encased within and running along the cord channel; and
the clamp comprises a first end portion where the cord enters the cord channel, a middle portion, and a second end portion where the cord exits the cord channel, wherein the first end portion and the second end portion each comprise an outwardly flared surface along an axis defined by the cord encased within and running along the cord channel;
whereby the outwardly flared surfaces enable the cord to bend and flex where the cord enters and exits the channel without fraying.

2. The anchor device of claim 1 wherein
the lower housing further comprises a lower housing major surface; and
the upper housing further comprises an upper housing major surface;
wherein the upper housing major surface substantially abuts the lower housing major surface when the upper housing is joined to the lower housing and provides a stop to prevent overtightening of the upper housing to the lower housing.

3. The anchor device of claim 2 wherein the lower housing major surface is flat and the upper housing major surface is flat.

4. The anchor device of claim 2 wherein
the lower housing further comprises a lower housing minor surface; and
the upper housing further comprises an upper housing minor surface;
wherein the upper housing minor surface substantially abuts the lower housing minor surface when the upper housing is joined to the lower housing and provides a stop to prevent overtightening of the upper housing to the lower housing.

5. The anchor device of claim 4 wherein the lower housing minor surface is flat and the upper housing minor surface is flat.

6. The anchor device of claim 4 wherein the cord channel is formed by adjoining the upper housing major surface to the lower housing major surface, the upper housing minor surface to the lower housing minor surface, and the clamp over the cradle.

7. The anchor device of claim 6 wherein the at least one cord encased within the cord channel is partially compressed by the adjoining of the clamp to the cradle.

8. The anchor device of claim 7 wherein the adjoining of the upper housing major surface to the lower housing major surface and the upper housing minor surface to the lower housing minor surface provides a limit to the compression of the at least one cord by the clamp over the cradle.

9. The anchor device of claim 1 wherein
the means for fastening comprises a threaded fastener;
the lower housing further comprises a receiving cylindrical portion comprising threads suitable for receiving the threaded fastener; and
the upper housing further comprises an aperture for receiving therethrough the threaded fastener.

10. The anchor device of claim 9 wherein
the threaded fastener is a screw comprising a head, and
the aperture in the upper housing is countersunk to allow the head of the screw to be substantially flush with the upper housing.

11. The anchor device of claim 10 wherein the screw is captively associated with the upper housing.

12. The anchor device of claim 1 wherein the cord housing is fixedly coupled to the post.

13. An anchor device for insertion into a bone, comprising
a post suitable for implantation into a bone, and
a cord housing coupled to the post, comprising
   a lower housing comprising a cradle for receiving therein at least one cord; and
   an upper housing comprising a clamp for placement over the at least one cord inserted into the cradle;
   wherein the joining of the upper housing to the lower housing forms a cord channel by the cradle and the clamp, to encase the at least one cord placed into the cradle; and
   means for fastening the upper housing to the lower housing and securing the at least one cord within the cord channel;
   wherein the cradle comprises a non-smooth surface suitable for gripping the at least one cord when inserted therewithin, wherein the non-smooth surface of the cradle comprises a plurality of ribs extending substantially perpendicular to the direction in which the cord is placed within the cradle,
   wherein the clamp comprises a non-smooth surface suitable for gripping the at least one cord when inserted therewithin, wherein the non-smooth surface of the clamp comprises a plurality of ribs extending substantially perpendicular to the direction in which the cord is placed within the cradle,
   whereby a locally compressive force is imparted on the cord so that the cord is held securely in place when the upper housing is joined to the lower housing around the cord and the cord is prevented from being pulled in either direction in the event there are stresses on the cord imparted during normal use.

14. The anchor device of claim 13 wherein
the lower housing further comprises a lower housing major surface; and
the upper housing further comprises an upper housing major surface;
wherein the upper housing major surface substantially abuts the lower housing major surface when the upper housing is joined to the lower housing and provides a stop to prevent overtightening of the upper housing to the lower housing.

15. The anchor device of claim 14 wherein the lower housing major surface is flat and the upper housing major surface is flat.

16. The anchor device of claim 14 wherein
the lower housing further comprises a lower housing minor surface; and
the upper housing further comprises an upper housing minor surface;
wherein the upper housing minor surface substantially abuts the lower housing minor surface when the upper housing is joined to the lower housing and provides a stop to prevent overtightening of the upper housing to the lower housing.

17. The anchor device of claim 16 wherein the lower housing minor surface is flat and the upper housing minor surface is flat.

18. The anchor device of claim 16 wherein the cord channel is formed by adjoining the upper housing major surface to the lower housing major surface, the upper housing minor surface to the lower housing minor surface, and the clamp over the cradle.

19. The anchor device of claim 18 wherein the at least one cord encased within the cord channel is partially compressed by the adjoining of the clamp to the cradle.

20. The anchor device of claim 19 wherein the adjoining of the upper housing major surface to the lower housing major surface and the upper housing minor surface to the lower housing minor surface provides a limit to the compression of the at least one cord by the clamp over the cradle.

21. The anchor device of claim 13 wherein
the means for fastening comprises a threaded fastener;
the lower housing further comprises a receiving cylindrical portion comprising threads suitable for receiving the threaded fastener; and
the upper housing further comprises an aperture for receiving therethrough the threaded fastener.

22. The anchor device of claim 21 wherein
the threaded fastener is a screw comprising a head, and
the aperture in the upper housing is countersunk to allow the head of the screw to be substantially flush with the upper housing.

23. The anchor device of claim 22 wherein the screw is captively associated with the upper housing.

24. The anchor device of claim 13 wherein the cord housing is fixedly coupled to the post.

25. An anchor device for insertion into a bone, comprising
a post suitable for implantation into a bone, and
a cord housing coupled to the post, comprising
   a lower housing comprising a cradle for receiving therein at least one cord; and
   an upper housing comprising a clamp for placement over the at least one cord inserted into the cradle;
   wherein the joining of the upper housing to the lower housing forms a cord channel by the cradle and the clamp, to encase the at least one cord placed into the cradle; and
   means for fastening the upper housing to the lower housing and securing the at least one cord within the cord channel
wherein
   the cradle is partially cylindrical and adapted to receive a single cord;
   the clamp is partially cylindrical and adapted for placement over the single cord inserted into the cradle; and
   the cord channel formed by clamp and the cradle when the upper housing is joined to the lower housing is substantially cylindrical to encase a single cord placed into the cradle;
   wherein the cradle provides a cross-sectional profile of greater than half of the cylinder and extends more than halfway around the cord, and the clamp provides a cross-sectional profile of less than half of the cylinder and extends less than halfway around the cord when placed over it;
   whereby the cord is press fit into the cradle with a small amount of force so the cord temporarily compresses to fit within the cradle and is held in place temporarily by the cradle until the upper housing is located in place with the clamp over the cradle and secures it with the means for fastening.

26. The anchor device of claim 25 wherein
the lower housing further comprises a lower housing major surface; and
the upper housing further comprises an upper housing major surface;
wherein the upper housing major surface substantially abuts the lower housing major surface when the upper housing is joined to the lower housing and provides a stop to prevent overtightening of the upper housing to the lower housing.

27. The anchor device of claim 26 wherein the lower housing major surface is flat and the upper housing major surface is flat.

28. The anchor device of claim 26 wherein
the lower housing further comprises a lower housing minor surface; and
the upper housing further comprises an upper housing minor surface;
wherein the upper housing minor surface substantially abuts the lower housing minor surface when the upper housing is joined to the lower housing and provides a stop to prevent overtightening of the upper housing to the lower housing.

29. The anchor device of claim 28 wherein the lower housing minor surface is flat and the upper housing minor surface is flat.

30. The anchor device of claim 28 wherein the cord channel is formed by adjoining the upper housing major surface to the lower housing major surface, the upper housing minor surface to the lower housing minor surface, and the clamp over the cradle.

31. The anchor device of claim 30 wherein the at least one cord encased within the cord channel is partially compressed by the adjoining of the clamp to the cradle.

32. The anchor device of claim 31 wherein the adjoining of the upper housing major surface to the lower housing major surface and the upper housing minor surface to the lower housing minor surface provides a limit to the compression of the at least one cord by the clamp over the cradle.

33. The anchor device of claim 25 wherein
the means for fastening comprises a threaded fastener;
the lower housing further comprises a receiving cylindrical portion comprising threads suitable for receiving the threaded fastener; and
the upper housing further comprises an aperture for receiving therethrough the threaded fastener.

34. The anchor device of claim 33 wherein
the threaded fastener is a screw comprising a head, and
the aperture in the upper housing is countersunk to allow the head of the screw to be substantially flush with the upper housing.

35. The anchor device of claim 34 wherein the screw is captively associated with the upper housing.

36. The anchor device of claim 25 wherein the cord housing is fixedly coupled to the post.

* * * * *